United States Patent
Kurokawa et al.

(10) Patent No.: US 9,972,655 B2
(45) Date of Patent: May 15, 2018

(54) IMAGING DEVICE AND METHOD FOR DRIVING THE SAME

(71) Applicant: SEMICONDUCTOR ENERGY LABORATORY CO., LTD., Atsugi-shi, Kanagawa-ken (JP)

(72) Inventors: Yoshiyuki Kurokawa, Kanagawa (JP); Takayuki Ikeda, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 645 days.

(21) Appl. No.: 14/483,457

(22) Filed: Sep. 11, 2014

(65) Prior Publication Data

US 2015/0028335 A1     Jan. 29, 2015

Related U.S. Application Data

(63) Continuation of application No. 13/965,265, filed on Aug. 13, 2013, now Pat. No. 8,872,120.

(30) Foreign Application Priority Data

Aug. 23, 2012 (JP) .................................. 2012-184295

(51) Int. Cl.
    *H01L 27/146*     (2006.01)
    *A61B 6/00*     (2006.01)
    *H01L 27/12*     (2006.01)
    *H01L 31/0376*     (2006.01)
    *H04N 5/32*     (2006.01)
    *H04N 5/3745*     (2011.01)

(52) U.S. Cl.
    CPC ...... *H01L 27/14663* (2013.01); *A61B 6/4208* (2013.01); *H01L 27/1225* (2013.01);
(Continued)

(58) Field of Classification Search
    CPC ........... H01L 27/14663; H01L 27/1225; H01L 27/14669; H01L 27/14643; H01L 29/7869;
(Continued)

(56) References Cited

U.S. PATENT DOCUMENTS 4,724,323 A     2/1988    Fukaya et al.
4,746,535 A     5/1988    Fukuyama et al.
(Continued)

FOREIGN PATENT DOCUMENTS

CN     101509977 A     8/2009
CN     102420945 A     4/2012
(Continued)

OTHER PUBLICATIONS

Jeon.S et al., "180nm Gate Length Amorphous InGaZnO Thin Film Transistor for High Density Image Sensor Applications", IEDM 10: Technical Digest of International Electron Devices Meeting, Dec. 6, 2010, pp. 504-507.

(Continued)

*Primary Examiner* — David Porta
*Assistant Examiner* — Djura Malevic
(74) *Attorney, Agent, or Firm* — Nixon Peabody LLP; Jeffery L. Costellia

(57) ABSTRACT

An imaging device capable of obtaining image data with a small amount of X-ray irradiation is provided. The imaging device obtains an image using X-rays and includes a scintillator and a plurality of pixel circuits arranged in a matrix and overlapping with the scintillator. The use of a transistor with an extremely small off-state current in the pixel circuits enables leakage of electrical charges from a charge accumulation portion to be reduced as much as possible, and an accumulation operation to be performed substantially at the same time in all of the pixel circuits. The accumulation operation is synchronized with X-ray irradiation, so that the amount of X-ray irradiation can be reduced.

20 Claims, 13 Drawing Sheets

(52) U.S. Cl.
CPC .... *H01L 27/1255* (2013.01); *H01L 27/14612* (2013.01); *H01L 31/0376* (2013.01); *H04N 5/32* (2013.01); *H04N 5/3745* (2013.01)

(58) Field of Classification Search
CPC .. H04N 5/30; H04N 5/32; H04N 5/33; H04N 5/335
See application file for complete search history.

(56) References Cited

U.S. PATENT DOCUMENTS

| | | | |
|---|---|---|---|
| 5,731,856 A | 3/1998 | Kim et al. | |
| 5,744,864 A | 4/1998 | Cillessen et al. | |
| 6,294,274 B1 | 9/2001 | Kawazoe et al. | |
| 6,563,174 B2 | 5/2003 | Kawasaki et al. | |
| 6,727,522 B1 | 4/2004 | Kawasaki et al. | |
| 6,747,638 B2 | 6/2004 | Yamazaki et al. | |
| 6,787,778 B2 | 9/2004 | Kobayashi et al. | |
| 7,049,190 B2 | 5/2006 | Takeda et al. | |
| 7,061,014 B2 | 6/2006 | Hosono et al. | |
| 7,064,346 B2 | 6/2006 | Kawasaki et al. | |
| 7,105,868 B2 | 9/2006 | Nause et al. | |
| 7,211,825 B2 | 5/2007 | Shih et al. | |
| 7,271,835 B2 | 9/2007 | Iizuka et al. | |
| 7,282,782 B2 | 10/2007 | Hoffman et al. | |
| 7,297,977 B2 | 11/2007 | Hoffman et al. | |
| 7,323,356 B2 | 1/2008 | Hosono et al. | |
| 7,385,224 B2 | 6/2008 | Ishii et al. | |
| 7,402,506 B2 | 7/2008 | Levy et al. | |
| 7,411,209 B2 | 8/2008 | Endo et al. | |
| 7,453,065 B2 | 11/2008 | Saito et al. | |
| 7,453,087 B2 | 11/2008 | Iwasaki | |
| 7,462,862 B2 | 12/2008 | Hoffman et al. | |
| 7,468,304 B2 | 12/2008 | Kaji et al. | |
| 7,501,293 B2 | 3/2009 | Ito et al. | |
| 7,525,523 B2 | 4/2009 | Yamazaki et al. | |
| 7,674,650 B2 | 3/2010 | Akimoto et al. | |
| 7,732,819 B2 | 6/2010 | Akimoto et al. | |
| 7,745,798 B2 | 6/2010 | Takahashi | |
| 8,067,745 B2 | 11/2011 | Jung et al. | |
| 8,368,027 B2 * | 2/2013 | Ishii | G01T 1/2018 250/366 |
| 8,461,545 B2 | 6/2013 | Imai | |
| 8,461,590 B2 | 6/2013 | Tamura et al. | |
| 8,492,728 B2 * | 7/2013 | Antonuk | H01L 27/1462 250/361 R |
| 8,519,320 B2 | 8/2013 | Miyazawa et al. | |
| 9,473,714 B2 | 10/2016 | Aoki et al. | |
| 2001/0046027 A1 | 11/2001 | Tai et al. | |
| 2002/0056838 A1 | 5/2002 | Ogawa | |
| 2002/0132454 A1 | 9/2002 | Ohtsu et al. | |
| 2003/0189401 A1 | 10/2003 | Kido et al. | |
| 2003/0218222 A1 | 11/2003 | Wager, III et al. | |
| 2004/0038446 A1 | 2/2004 | Takeda et al. | |
| 2004/0127038 A1 | 7/2004 | Carcia et al. | |
| 2005/0017302 A1 | 1/2005 | Hoffman | |
| 2005/0199959 A1 | 9/2005 | Chiang et al. | |
| 2005/0231656 A1 | 10/2005 | Den Boer et al. | |
| 2006/0035452 A1 | 2/2006 | Carcia et al. | |
| 2006/0043377 A1 | 3/2006 | Hoffman et al. | |
| 2006/0091793 A1 | 5/2006 | Baude et al. | |
| 2006/0108529 A1 | 5/2006 | Saito et al. | |
| 2006/0108636 A1 | 5/2006 | Sano et al. | |
| 2006/0110867 A1 | 5/2006 | Yabuta et al. | |
| 2006/0113536 A1 | 6/2006 | Kumomi et al. | |
| 2006/0113539 A1 | 6/2006 | Sano et al. | |
| 2006/0113549 A1 | 6/2006 | Den et al. | |
| 2006/0113565 A1 | 6/2006 | Abe et al. | |
| 2006/0157760 A1 | 7/2006 | Hayashi et al. | |
| 2006/0169973 A1 | 8/2006 | Isa et al. | |
| 2006/0170111 A1 | 8/2006 | Isa et al. | |
| 2006/0197092 A1 | 9/2006 | Hoffman et al. | |
| 2006/0208977 A1 | 9/2006 | Kimura | |
| 2006/0228974 A1 | 10/2006 | Thelss et al. | |
| 2006/0231882 A1 | 10/2006 | Kim et al. | |
| 2006/0238135 A1 | 10/2006 | Kimura | |
| 2006/0244107 A1 | 11/2006 | Sugihara et al. | |
| 2006/0284171 A1 | 12/2006 | Levy et al. | |
| 2006/0284172 A1 | 12/2006 | Ishii | |
| 2006/0292777 A1 | 12/2006 | Dunbar | |
| 2007/0018075 A1 | 1/2007 | Cazaux et al. | |
| 2007/0024187 A1 | 2/2007 | Shin et al. | |
| 2007/0035653 A1 * | 2/2007 | Hong | G06T 5/50 348/340 |
| 2007/0046191 A1 | 3/2007 | Saito | |
| 2007/0052025 A1 | 3/2007 | Yabuta | |
| 2007/0054507 A1 | 3/2007 | Kaji et al. | |
| 2007/0090365 A1 | 4/2007 | Hayashi et al. | |
| 2007/0108446 A1 | 5/2007 | Akimoto | |
| 2007/0152217 A1 | 7/2007 | Lai et al. | |
| 2007/0172591 A1 | 7/2007 | Seo et al. | |
| 2007/0187678 A1 | 8/2007 | Hirao et al. | |
| 2007/0187760 A1 | 8/2007 | Furuta et al. | |
| 2007/0194379 A1 | 8/2007 | Hosono et al. | |
| 2007/0252928 A1 | 11/2007 | Ito et al. | |
| 2007/0272922 A1 | 11/2007 | Kim et al. | |
| 2007/0287296 A1 | 12/2007 | Chang | |
| 2008/0001179 A1 | 1/2008 | Roy | |
| 2008/0006877 A1 | 1/2008 | Mardilovich et al. | |
| 2008/0038882 A1 | 2/2008 | Takechi et al. | |
| 2008/0038929 A1 | 2/2008 | Chang | |
| 2008/0050595 A1 | 2/2008 | Nakagawara et al. | |
| 2008/0054319 A1 | 3/2008 | Mouli | |
| 2008/0073653 A1 | 3/2008 | Iwasaki | |
| 2008/0083950 A1 | 4/2008 | Pan et al. | |
| 2008/0106191 A1 | 5/2008 | Kawase | |
| 2008/0128689 A1 | 6/2008 | Lee et al. | |
| 2008/0129195 A1 | 6/2008 | Ishizaki et al. | |
| 2008/0166834 A1 | 7/2008 | Kim et al. | |
| 2008/0182358 A1 | 7/2008 | Cowdery-Corvan et al. | |
| 2008/0224133 A1 | 9/2008 | Park et al. | |
| 2008/0254569 A1 | 10/2008 | Hoffman et al. | |
| 2008/0258139 A1 | 10/2008 | Ito et al. | |
| 2008/0258140 A1 | 10/2008 | Lee et al. | |
| 2008/0258141 A1 | 10/2008 | Park et al. | |
| 2008/0258143 A1 | 10/2008 | Kim et al. | |
| 2008/0296568 A1 | 12/2008 | Ryu et al. | |
| 2009/0040310 A1 * | 2/2009 | Nomura | H01L 27/14603 348/162 |
| 2009/0068773 A1 | 3/2009 | Lai et al. | |
| 2009/0073325 A1 | 3/2009 | Kuwabara et al. | |
| 2009/0101948 A1 | 4/2009 | Park et al. | |
| 2009/0114910 A1 | 5/2009 | Chang | |
| 2009/0134399 A1 | 5/2009 | Sakakura et al. | |
| 2009/0152506 A1 | 6/2009 | Umeda et al. | |
| 2009/0152541 A1 | 6/2009 | Maekawa et al. | |
| 2009/0278122 A1 | 11/2009 | Hosono et al. | |
| 2009/0280600 A1 | 11/2009 | Hosono et al. | |
| 2009/0295769 A1 | 12/2009 | Yamazaki et al. | |
| 2009/0302229 A1 | 12/2009 | Watanabe et al. | |
| 2010/0065844 A1 | 3/2010 | Tokunaga | |
| 2010/0092800 A1 | 4/2010 | Itagaki et al. | |
| 2010/0109002 A1 | 5/2010 | Itagaki et al. | |
| 2010/0117991 A1 * | 5/2010 | Koyama | G02F 1/13338 345/175 |
| 2010/0182282 A1 * | 7/2010 | Kurokawa | G02F 1/13338 345/175 |
| 2011/0064195 A1 * | 3/2011 | Kyushima | A61B 6/032 378/62 |
| 2011/0109299 A1 * | 5/2011 | Chaji | G09G 3/3283 324/76.11 |
| 2011/0109612 A1 * | 5/2011 | Chaji | G09G 3/3283 345/211 |
| 2011/0176038 A1 * | 7/2011 | Kurokawa | H04N 5/3696 348/294 |
| 2011/0215323 A1 * | 9/2011 | Kurokawa | H01L 27/14603 257/53 |
| 2011/0220889 A1 * | 9/2011 | Kurokawa | G02F 1/1362 257/43 |
| 2011/0221723 A1 * | 9/2011 | Kurokawa | G06F 3/042 345/207 |
| 2011/0299654 A1 * | 12/2011 | Mori | A61B 6/032 378/62 |

(56) References Cited

U.S. PATENT DOCUMENTS

| | | | |
|---|---|---|---|
| 2011/0303849 A1* | 12/2011 | Tredwell | G01T 1/2018 250/362 |
| 2012/0002090 A1* | 1/2012 | Aoki | G09G 3/3413 348/297 |
| 2012/0032193 A1* | 2/2012 | Kurokawa | H01L 27/14632 257/84 |
| 2012/0049078 A1 | 3/2012 | Senda et al. | |
| 2012/0056861 A1* | 3/2012 | Kurokawa | G09G 3/3648 345/207 |
| 2012/0126124 A1 | 5/2012 | Nakatsugawa et al. | |
| 2012/0126129 A1 | 5/2012 | Nakatsugawa et al. | |
| 2012/0161018 A1 | 6/2012 | Shin | |
| 2012/0193542 A1 | 8/2012 | Yamada | |
| 2012/0201350 A1 | 8/2012 | Kim | |
| 2013/0037699 A1 | 2/2013 | Ihori et al. | |
| 2013/0082184 A1* | 4/2013 | Nakatsugawa | A61B 6/4208 250/366 |

FOREIGN PATENT DOCUMENTS

| | | |
|---|---|---|
| CN | 102859992 A | 1/2013 |
| EP | 0177044 A | 4/1986 |
| EP | 1737044 A | 12/2006 |
| EP | 2090901 A | 8/2009 |
| EP | 2226847 A | 9/2010 |
| EP | 2560372 A | 2/2013 |
| JP | 60-198861 A | 10/1985 |
| JP | 61-089659 A | 5/1986 |
| JP | 63-210022 A | 8/1988 |
| JP | 63-210023 A | 8/1988 |
| JP | 63-210024 A | 8/1988 |
| JP | 63-215519 A | 9/1988 |
| JP | 63-239117 A | 10/1988 |
| JP | 63-265818 A | 11/1988 |
| JP | 05-251705 A | 9/1993 |
| JP | 08-264794 A | 10/1996 |
| JP | 11-505377 | 5/1999 |
| JP | 11-311673 A | 11/1999 |
| JP | 2000-044236 A | 2/2000 |
| JP | 2000-150900 A | 5/2000 |
| JP | 2002-076356 A | 3/2002 |
| JP | 2002-246580 A | 8/2002 |
| JP | 2002-289859 A | 10/2002 |
| JP | 2003-086000 A | 3/2003 |
| JP | 2003-086808 A | 3/2003 |
| JP | 2004-103957 A | 4/2004 |
| JP | 2004-111590 A | 4/2004 |
| JP | 2004-273614 A | 9/2004 |
| JP | 2004-273732 A | 9/2004 |
| JP | 2006-191236 A | 7/2006 |
| JP | 2011-019102 A | 1/2011 |
| JP | 2011-114229 A | 6/2011 |
| JP | 2011-223508 A | 11/2011 |
| JP | 2011-247881 A | 12/2011 |
| JP | 2012-034354 A | 2/2012 |
| JP | 2012-047516 A | 3/2012 |
| JP | 2012-256812 A | 12/2012 |
| JP | 2012-256819 A | 12/2012 |
| KR | 2012-0025988 A | 3/2012 |
| TW | 201234850 | 8/2012 |
| TW | 201246591 | 11/2012 |
| WO | WO-2004/114391 | 12/2004 |
| WO | WO-2011/129143 | 10/2011 |

OTHER PUBLICATIONS

Fortunato.E et al., "Wide-Bandgap High-Mobility ZnO Thin-Film Transistors Produced at Room Temperature", Appl. Phys. Lett. (Applied Physics Letters), Sep. 27, 2004, vol. 85, No. 13, pp. 2541-2543.

Dembo.H et al., "RFCPUS on Glass and Plastic Substrates Fabricated by TFT Transfer Technology", IEDM 05: Technical Digest of International Electron Devices Meeting, Dec. 5, 2005, pp. 1067-1069.

Ikeda.T et al., "Full-Functional System Liquid Crystal Display Using Cg-Silicon Technology", SID Digest '04: SID International Symposium Digest of Technical Papers, 2004, vol. 35, pp. 860-863.

Nomura.K et al., "Room-Temperature Fabrication of Transparent Flexible Thin-Film Transistors Using Amorphous Oxide Semiconductors", Nature, Nov. 25, 2004, vol. 432, pp. 488-492.

Park.J et al., "Improvements in the Device Characteristics of Amorphous Indium Gallium Zinc Oxide Thin-Film Transistors by Ar Plasma Treatment", Appl. Phys. Lett. (Applied Physics Letters), Jun. 26, 2007, vol. 90, No. 26, pp. 262106-1-262106-3.

Takahashi.M et al., "Theoretical Analysis of IGZO Transparent Amorphous Oxide Semiconductor", IDW '08: Proceedings of the 15th International Display Workshops, Dec. 3, 2008, pp. 1637-1640.

Hayashi.R et al., "42.1: Invited Paper: Improved Amorphous In—Ga—Zn—O TFTs", SID Digest '08: SID International Symposium Digest of Technical Papers, May 20, 2008, vol. 39, pp. 621-624.

Prins.M et al., "A Ferroelectric Transparent Thin-Film Transistor", Appl. Phys. Lett. (Applied Physics Letters), Jun. 17, 1996, vol. 68, No. 25, pp. 3650-3652.

Nakamura.M et al., "The phase relations in the In2O3—Ga2ZnO4—ZnO system at 1350°C.", Journal of Solid State Chemistry, Aug. 1, 1991, vol. 93, No. 2, pp. 298-315.

Kimizuka.N et al., "Syntheses and Single-Crystal Data of Homologous Compounds, In2O3(ZnO)m (m=3, 4, and 5), InGaO3(ZnO)3, and Ga2O3(ZnO)m (m=7, 8, 9, and 16) in the In2O3—ZnGa2O4—ZnO System", Journal of Solid State Chemistry, Apr. 1, 1995, vol. 116, No. 1, pp. 170-178.

Nomura.K et al., "Thin-Film Transistor Fabricated in Single-Crystalline Transparent Oxide Semiconductor", Science, May 23, 2003, vol. 300, No. 5623, pp. 1269-1272.

Masuda.S et al., "Transparent thin film transistors using ZnO as an active channel layer and their electrical properties", J. Appl. Phys. (Journal of Applied Physics), Feb. 1, 2003, vol. 93, No. 3, pp. 1624-1630.

Asakuma.N et al., "Crystallization and Reduction of Sol-Gel-Derived Zinc Oxide Films by Irradiation With Ultraviolet Lamp", Journal of Sol-Gel Science and Technology, 2003, vol. 26, pp. 181-184.

Osada.T et al., "15.2: Development of Driver-Integrated Panel using Amorphous In—Ga—Zn-Oxide TFT", SID Digest '09: SID International Symposium Digest of Technical Papers, May 31, 2009, pp. 184-187.

Nomura.K et al., "Carrier transport in transparent oxide semiconductor with intrinsic structural randomness probed using single-crystalline InGaO3(ZnO)5 films", Appl. Phys. Lett. (Applied Physics Letters), Sep. 13, 2004, vol. 85, No. 11, pp. 1993-1995.

Li.C et al., "Modulated Structures of Homologous Compounds InMo3(ZnO)m (M=In,Ga; m=Integer) Described by Four-Dimensional Superspace Group", Journal of Solid State Chemistry, 1998, vol. 139, pp. 347-355.

Son.K et al., "42.4L: Late-News Paper: 4 Inch QVGA AMOLED Driven by the Threshold Voltage Controlled Amorphous GIZO (Ga2O3—In2O3—ZnO) TFT", SID Digest '08: SID International Symposium Digest of Technical Papers, May 20, 2008, vol. 39, pp. 633-636.

Lee.J et al., "World's Largest (15-Inch) XGA AMLCD Panel Using IGZO Oxide TFT", SID Digest '08: SID International Symposium Digest of Technical Papers, May 20, 2008, vol. 39, pp. 625-628.

Nowatari.H et al., "60.2: Intermediate Connector With Suppressed Voltage Loss for White Tandem OLEDs", SID Digest '09: SID International Symposium Digest of Technical Papers, May 31, 2009, vol. 40, pp. 899-902.

Kanno.H et al., "White Stacked Electrophosphorecent Organic Light-Emitting Devices Employing MoO3 as a Charge-Generation Layer", Adv. Mater. (Advanced Materials), 2006, vol. 18, No. 3, pp. 339-342.

Tsuda.K et al., "Ultra Low Power Consumption Technologies for Mobile TFT-LCDs ", IDW '02: Proceedings of the 9th International Display Workshops, Dec. 4, 2002, pp. 295-298.

(56) References Cited

OTHER PUBLICATIONS

Van de Walle.C, "Hydrogen as a Cause of Doping in Zinc Oxide", Phys. Rev. Lett. (Physical Review Letters), Jul. 31, 2000, vol. 85, No. 5, pp. 1012-1015.

Fung.T et al., "2-D Numerical Simulation of High Performance Amorphous In—Ga—Zn—O TFTs for Flat Panel Displays", AM-FPD '08 Digest of Technical Papers, Jul. 2, 2008, pp. 251-252, The Japan Society of Applied Physics.

Jeong.J et al., "3.1: Distinguished Paper: 12.1-Inch WXGA AMOLED Display Driven by Indium-Gallium-Zinc Oxide TFTs Array", SID Digest '08: SID International Symposium Digest of Technical Papers, May 20, 2008, vol. 39, No. 1, pp. 1-4.

Park.J et al., "High performance amorphous oxide thin film transistors with self-aligned top-gate structure", IEDM 09: Technical Digest of International Electron Devices Meeting, Dec. 7, 2009, pp. 191-194.

Kurokawa.Y et al., "UHF RFCPUS on Flexible and Glass Substrates for Secure RFID Systems", Journal of Solid-State Circuits, 2008, vol. 43, No. 1, pp. 292-299.

Ohara.H et al., "Amorphous In—Ga—Zn-Oxide TFTs with Suppressed Variation for 4.0 inch QVGA AMOLED Display", AM-FPD '09 Digest of Technical Papers, Jul. 1, 2009, pp. 227-230, The Japan Society of Applied Physics.

Coates.D et al., "Optical Studies of the Amorphous Liquid-Cholesteric Liquid Crystal Transition:The "Blue Phase"", Physics Letters, Sep. 10, 1973, vol. 45A, No. 2, pp. 115-116.

Cho.D et al., "21.2:Al and Sn-Doped Zinc Indium Oxide Thin Film Transistors for AMOLED Back Plane", SID Digest '09: SID International Symposium Digest of Technical Papers, May 31, 2009, pp. 280-283.

Lee.M et al., "15.4:Excellent Performance of Indium-Oxide-Based Thin-Film Transistors by DC Sputtering", SID Digest '09: SID International Symposium Digest of Technical Papers, May 31, 2009, pp. 191-193.

Jin.D et al., "65.2:Distinguished Paper:World-Largest (6.5") Flexible Full Color Top Emission AMOLED Display on Plastic Film and its Bending Properties", SID Digest '09: SID International Symposium Digest of Technical Papers, May 31, 2009, pp. 983-985.

Sakata.J et al., "Development of 4.0-In. AMOLED Display With Driver Circuit Using Amorphous In—Ga—Zn-Oxide TFTs", IDW '09: Proceedings of the 16th International Display Workshops, 2009, pp. 689-692.

Park.J et al., "Amorphous Indium-Gallium-Zinc Oxide TFTs and Their Application for Large Size AMOLED", AM-FPD '08 Digest of Technical Papers, Jul. 2, 2008, pp. 275-278.

Park.S et al., "Challenge to Future Displays: Transparent AM-OLED Driven by PEALD Grown ZnO TFT", IMID '07 Digest, 2007, pp. 1249-1252.

Godo.H et al., "Temperature Dependence of Characteristics and Electronic Structure for Amorphous In—Ga—Zn-Oxide TFT", AM-FPD '09 Digest of Technical Papers, Jul. 1, 2009, pp. 41-44.

Osada.T et al., "Development of Driver-Integrated Panel Using Amorphous In—Ga—Zn-Oxide TFT", AM-FPD '09 Digest of Technical Papers, Jul. 1, 2009, pp. 33-36.

Hirao.T et al., "Novel Top-Gate Zinc Oxide Thin-Film Transistors (ZnO TFTs) for AMLCDs", J. Soc. Inf. Display (Journal of the Society for Information Display), 2007, vol. 15, No. 1, pp. 17 22.

Hosono.H, "68.3:Invited Paper:Transparent Amorphous Oxide Semiconductors for High Performance TFT", SID Digest '07: SID International Symposium Digest of Technical Papers, 2007, vol. 38, pp. 1830-1833.

Godo.H et al., "P-9:Numerical Analysis on Temperature Dependence of Characteristics of Amorphous In—Ga—Zn-Oxide TFT", SID Digest '09: SID International Symposium Digest of Technical Papers, May 31, 2009, pp. 1110-1112.

Ohara.H et al., "21.3:4.0 In. QVGA AMOLED Display Using In—Ga—Zn-Oxide TFTs With a Novel Passivation Layer", SID Digest '09: SID International Symposium Digest of Technical Papers, May 31, 2009, pp. 284-287.

Miyasaka.M, "SUFTLA Flexible Microelectronics on Their Way to Business", SID Digest '07: SID International Symposium Digest of Technical Papers, 2007, vol. 38, pp. 1673-1676.

Chern.H et al., "An Analytical Model for the Above-Threshold Characteristics of Polysilicon Thin-Film Transistors", IEEE Transactions on Electron Devices, Jul. 1, 1995, vol. 42, No. 7, pp. 1240-1246.

Kikuchi.H et al., "39.1:Invited Paper:Optically Isotropic Nano-Structured Liquid Crystal Composites for Display Applications", SID Digest '09: SID International Symposium Digest of Technical Papers, May 31, 2009, pp. 578-581.

Asaoka.Y et al., "29.1:Polarizer-Free Reflective LCD Combined With Ultra Low-Power Driving Technology", SID Digest '09: SID International Symposium Digest of Technical Papers, May 31, 2009, pp. 395-398.

Lee.H et al., "Current Status of, Challenges to, and Perspective View of AM-OLED", IDW '06: Proceedings of the 13th International Display Workshops, Dec. 7, 2006, pp. 663-666.

Kikuchi.H et al., "62.2:Invited Paper:Fast Electro-Optical Switching in Polymer-Stabilized Liquid Crystal Blue Phases for Display Application", SID Digest '07: SID International Symposium Digest of Technical Papers, 2007, vol. 38, pp. 1737-1740.

Nakamura.M, "Synthesis of Homologous Compound with New Long-Period Structure", NIRIM Newsletter, Mar. 1, 1995, vol. 150, pp. 1-4.

Kikuchi.H et al., "Polymer-Stabilized Liquid Crystal Blue Phases", Nature Materials, Sep. 2, 2002, vol. 1, pp. 64-68.

Kimizuka.N et al., "Spinel,YbFe2O4, and Yb2Fe3O7 Types of Structures for Compounds in the In2O3 and Sc2O3—A2O3—BO Systems [A: Fe, Ga, or Al; B: Mg, Mn, Fe, Ni, Cu, or Zn] at Temperatures Over 1000° C.", Journal of Solid State Chemistry, 1985, vol. 60, pp. 382-384.

Kitzerow.H et al., "Observation of Blue Phases in Chiral Networks", Liquid Crystals, 1993, vol. 14, No. 3, pp. 911-916.

Costello.M et al., "Electron Microscopy of a Cholesteric Liquid Crystal and Its Blue Phase", Phys. Rev. A (Physical Review. A), May 1, 1984, vol. 29, No. 5, pp. 2957-2959.

Meiboom.S et al., "Theory of the Blue Phase of Cholesteric Liquid Crystals", Phys. Rev. Lett. (Physical Review Letters), May 4, 1981, vol. 46, No. 18, pp. 1216-1219.

Park.Sang-Hee et al., "42.3: Transparent ZnO Thin Film Transistor for the Application of High Aperture Ratio Bottom Emission AM-OLED Display", SID Digest '08: SID International Symposium Digest of Technical Papers, May 20, 2008, vol. 39, pp. 629-632.

Orita.M et al., "Mechanism of Electrical Conductivity of Transparent InGaZnO4", Phys. Rev B (Physical Review. B), Jan. 15, 2000, vol. 61, No. 3, pp. 1811-1816.

Nomura.K et al., "Amorphous Oxide Semiconductors for High-Performance Flexible Thin-Film Transistors", Jpn. J. Appl. Phys. (Japanese Journal of Applied Physics), 2006, vol. 45, No. 5B, pp. 4303-4308.

Janotti.A et al., "Native Point Defects in ZnO", Phys. Rev. B (Physical Review. B), Oct. 4, 2007, vol. 76, No. 16, pp. 165202-1-165202-22.

Park.J et al., "Electronic Transport Properties of Amorphous Indium-Gallium-Zinc Oxide Semiconductor Upon Exposure to Water", Appl. Phys. Lett. (Applied Physics Letters), 2008, vol. 92, pp. 072104-1-072104-3.

Hsieh.H et al., "P-29:Modeling of Amorphous Oxide Semiconductor Thin Film Transistors and Subgap Density of States", SID Digest '08: SID International Symposium Digest of Technical Papers, May 20, 2008, vol. 39, pp. 1277-1280.

Janotti.A et al., "Oxygen Vacancies in ZnO", Appl. Phys. Lett. (Applied Physics Letters), 2005, vol. 87, pp. 122102-1-122102-3.

Oba.F et al., "Defect energetics in ZnO: A hybrid Hartree-Fock density functional study", Phys. Rev. B (Physical Review. B), 2008, vol. 77, pp. 245202-1-245202-6.

Orita.M et al., "Amorphous transparent conductive oxide InGaO3(ZnO)m (m<4):a Zn4s conductor", Philosophical Magazine, 2001, vol. 81, No. 5, pp. 501-515.

(56) References Cited

OTHER PUBLICATIONS

Hosono.H et al., "Working hypothesis to explore novel wide band gap electrically conducting amorphous oxides and examples", J. Non-Cryst. Solids (Journal of Non-Crystalline Solids), 1996, vol. 198-200, pp. 165-169.

Mo.Y et al., "Amorphous Oxide TFT Backplanes for Large Size AMOLED Displays", IDW '08: Proceedings of the 6th International Display Workshops, Dec. 3, 2008, pp. 581-584.

Kim.S et al., "High-Performance oxide thin film transistors passivated by various gas plasmas", 214th ECS Meeting, 2008, No. 2317, ECS.

Clark.S et al., "First Principles Methods Using CASTEP", Zeitschrift fur Kristallographie, 2005, vol. 220, pp. 567-570.

Lany.S et al., "Dopability, Intrinsic Conductivity, and Nonstoichiometry of Transparent Conducting Oxides", Phys. Rev. Lett. (Physical Review Letters), Jan. 26, 2007, vol. 98, pp. 045501-1-045501-4.

Park.J et al., "Dry etching of ZnO films and plasma-induced damage to optical properties", J. Vac. Sci. Technol. B (Journal of Vacuum Science & Technology B), Mar. 1, 2003, vol. 21, No. 2, pp. 800-803.

Oh.M et al., "Improving the Gate Stability of ZnO Thin-Film Transistors With Aluminum Oxide Dielectric Layers", J. Electrochem. Soc. (Journal of the Electrochemical Society), 2008, vol. 155, No. 12, pp. H1009-H1014.

Ueno.K et al., "Field-Effect Transistor on SrTiO3 With Sputtered Al2O3 Gate Insulator", Appl. Phys. Lett. (Applied Physics Letters), Sep. 1, 2003, vol. 83, No. 9, pp. 1755-1757.

International Search Report (Application No. PCT/JP2013/072933) dated Oct. 22, 2013.

Written Opinion (Application No. PCT/JP2013/072933) dated Oct. 22, 2013.

Taiwanese Office Action (Application No. 105143923) dated May 18, 2017.

Chinese Ofrce Action (Applcation No. 201380043503.0) dated Apr. 5, 2017.

* cited by examiner

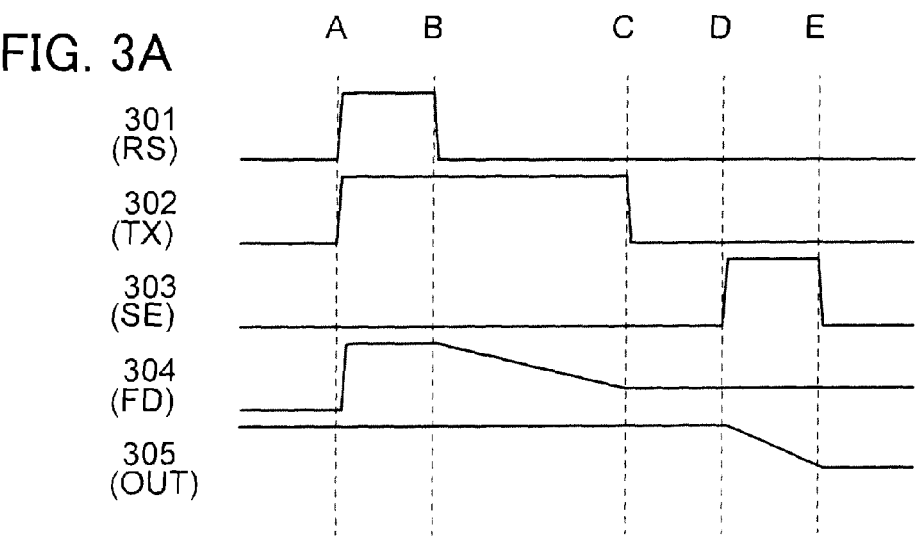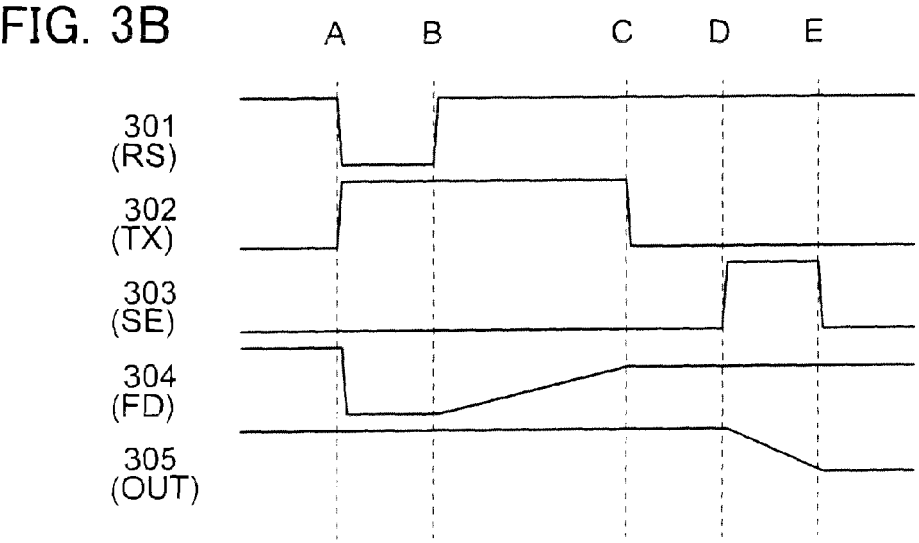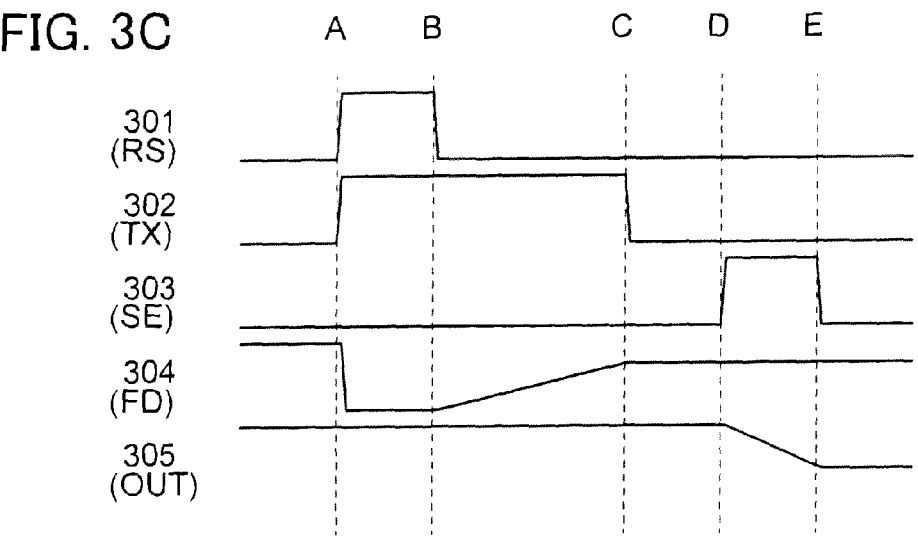

IMAGING DEVICE AND METHOD FOR DRIVING THE SAME

BACKGROUND OF THE INVENTION

1. Field of the Invention

One embodiment of the present invention relates to an imaging device including a scintillator and a method for driving the imaging device.

2. Description of the Related Art

In medical practice, a medical diagnostic imaging device using a photographic technique has been in wide use. With the medical diagnostic imaging device, a specific portion (e.g., bone or lungs) of a patient is irradiated with X-rays, an X-ray film is exposed to X-rays passing through the specific portion, and the X-ray film is developed to visualize a state inside the specific portion.

Since the method using X-ray films needs a storage space for the X-ray films and maintenance thereof is troublesome, digitization of images is in progress. As a method for digitizing images, a method using an imaging plate containing a material which emits light by being irradiated with X-rays (photostimulable material) has been known. By sensing light emitted from the imaging plate with scanner, digitized images can be obtained.

The imaging plate is a plate to which photostimulable phosphor is applied and which has higher sensitivity to X-ray absorption difference than X-ray films. Data of X-ray irradiation can be erased, so that the imaging plate can be re-used. However, data obtained by the imaging plate is analog, which requires a step for digitization.

For this reason, attention has been recently focused on flat panel detectors capable of obtaining digital data directly (e.g., Patent Document 1). Flat panel detectors have two systems, direct and indirect conversion systems. In the direct conversion system, X-rays are directly converted to electrical charges with the use of an X-ray detecting element. In the indirect conversion system, X-rays are converted to visible light with a scintillator and the light is converted to electrical charges by a photodiode. In either of the systems, a flat panel detector includes a plurality of pixel circuits arranged in a matrix.

REFERENCE

[Patent Document 1] Japanese Published Patent Application No. H11-311673

SUMMARY OF THE INVENTION

In diagnostic imaging using X-rays, X-ray exposure time for patients is preferably as short as possible in consideration of influence of X-rays on the human body. That is, an imaging device capable of obtaining image data by relatively short time irradiation with X-rays is desired.

Thus, one embodiment of the present invention is to provide an imaging device capable of obtaining image data with a relatively small amount of X-rays. Another object is to provide a method for driving the imaging device.

One embodiment of the present invention is an imaging device which obtains an image using X-rays and includes pixel circuits arranged in a matrix with plural rows and plural columns and overlapping with a scintillator. By using a transistor with an extremely small off-state current in the pixel circuits, leakage of electrical charges from a charge accumulation portion from the end of an accumulation period to the completion of reading the last row in a read period can be reduced as much as possible. Thus, an accumulation operation can be performed in all of the pixel circuits substantially at the same time, and the amount of X-ray irradiation can be reduced by synchronizing the accumulation operation with the X-ray irradiation.

One embodiment of the present invention is an imaging device including a scintillator and a plurality of pixel circuits that is arranged in a matrix with plural rows and plural columns and overlaps with the scintillator. The pixel circuits each include a photodiode, a charge accumulation portion, a first transistor, a second transistor, and a third transistor. One of a source and a drain of the first transistor is electrically connected to the photodiode. The other of the source and the drain of the first transistor is electrically connected to the charge accumulation portion. A gate of the second transistor is electrically connected to the charge accumulation portion. One of a source and a drain of the second transistor is electrically connected to one of a source and a drain of the third transistor. At least the first transistor includes a channel formation region formed of an oxide semiconductor. An operation of resetting the charge accumulation portion is performed substantially at the same time in the plurality of pixel circuits, an operation of accumulating an electrical charge by the photodiode is performed substantially at the same time in the plurality of pixel circuits, and then an operation of reading a signal is sequentially performed for each row in the plurality of pixel circuits.

Note that in this specification and the like, ordinal numbers such as "first" and "second" are used in order to avoid confusion among components and do not limit the components numerically.

Further, another embodiment of the present invention is an imaging device including a scintillator and a plurality of pixel circuits that is arranged in a matrix with plural rows and plural columns and overlaps with the scintillator. The pixel circuits each include an optical sensor element, a charge accumulation portion, a first transistor, a second transistor, a third transistor, and a fourth transistor. One of a source and a drain of the first transistor is electrically connected to the optical sensor element. The other of the source and the drain of the first transistor is electrically connected to the charge accumulation portion. A gate of the second transistor is electrically connected to the charge accumulation portion. One of a source and a drain of the second transistor is electrically connected to one of a source and a drain of the third transistor. One of a source and a drain of the fourth transistor is electrically connected to the charge accumulation portion. At least each of the first transistor and the fourth transistor includes a channel formation region formed of an oxide semiconductor. An operation of resetting the charge accumulation portion is performed substantially at the same time in the plurality of pixel circuits, an operation of accumulating an electrical charge by the optical sensor element is performed substantially at the same time in the plurality of pixel circuits, and then an operation of reading a signal is sequentially performed for each row in the plurality of pixel circuits.

For the optical sensor element, a photodiode can be used. Alternatively, the optical sensor element can have a structure including a pair of electrodes and an i-type amorphous silicon layer.

The second transistor and/or the third transistor may be a transistor including a channel formation region formed of an oxide semiconductor.

Furthermore, another embodiment of the present invention is a method for driving an imaging device including a scintillator and a plurality of pixel circuits that is arranged in a matrix with plural rows and plural columns and overlaps with the scintillator. The method for driving the imaging device includes a first step of performing an operation of resetting a charge accumulation portion included in each of the plurality of pixel circuits substantially at the same time, a second step of irradiating the scintillator with an X-ray so that an optical sensor element included in each of the plurality of pixel circuits is irradiated with light emitted from the scintillator, a third step of performing an operation of accumulating an electrical charge in the charge accumulation portion by the optical sensor element substantially at the same time, and a fourth step of sequentially performing an operation of reading a signal for each row in the plurality of pixel circuits. The second step is synchronized with the third step.

One embodiment of the present invention can provide an imaging device capable of obtaining image data with a relatively small amount of X-ray irradiation. Further, one embodiment of the present invention can provide a method for driving the imaging device.

BRIEF DESCRIPTION OF THE DRAWINGS

FIGS. 3A to 3C are timing charts each illustrating the operation of a pixel circuit.

DETAILED DESCRIPTION OF THE INVENTION

Figure 1:
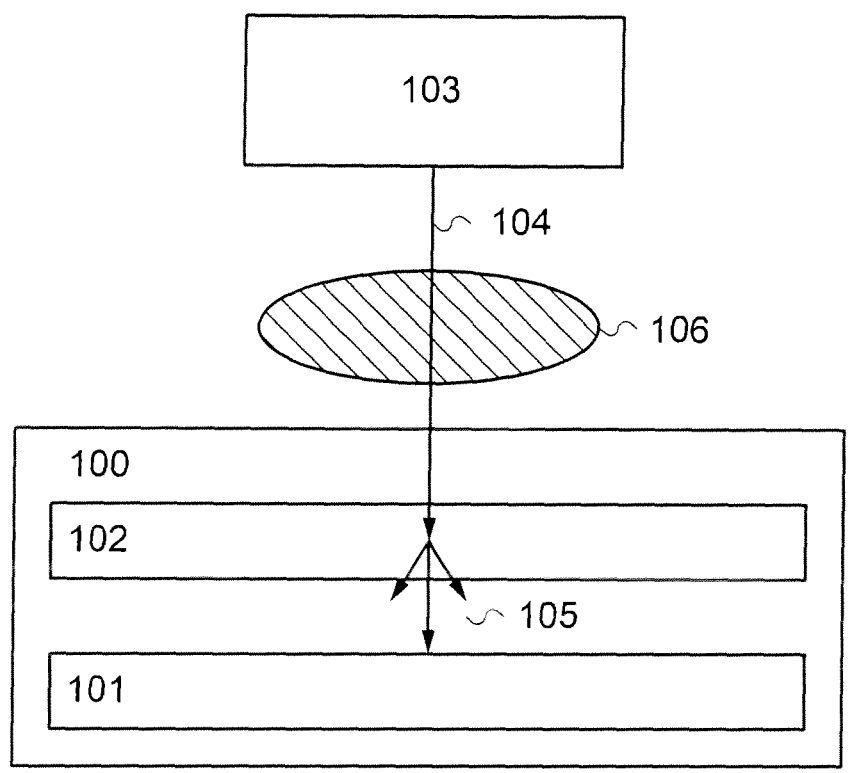
FIG. 1 illustrates an imaging device.

Embodiments of the present invention will be described below in detail with reference to the accompanying drawings. Note that the present invention is not limited to the description below, and it is easily understood by those skilled in the art that modes and details can be modified in various ways without departing from the spirit and scope of the present invention. Further, the present invention is not construed as being limited to description of the embodiments. Note that in all drawings used to illustrate the embodiments, portions that are identical or portions having similar functions are denoted by the same reference numerals, and their repetitive description may be omitted.

(Embodiment 1)

In this embodiment, an imaging device of one embodiment of the present invention is described with reference to the drawings.

An imaging device 100 illustrated in FIG. 1 includes a sensor substrate 101 including an optical sensor and a scintillator 102 converting radiation such as X-rays to visible light. The sensor substrate 101 and the scintillator 102 overlap with each other. An X-ray 104 is emitted from an X-ray source 103 to the scintillator 102 through an object 106, and is converted to visible light 105. The visible light is sensed by the optical sensor included in the sensor substrate 101, whereby image data is obtained.

The scintillator 102 is formed of a substance which absorbs energy of radiation such as X-rays or γ-rays to emit visible light or a material containing the substance. For example, materials such as $Gd_2O_2S{:}Tb$, $Gd_2O_2S{:}Pr$, $Gd_2O_2S{:}Eu$, and $BaFCl{:}Eu$ and a resin or ceramics in which any of the materials is dispersed are known.

Figure 2A:
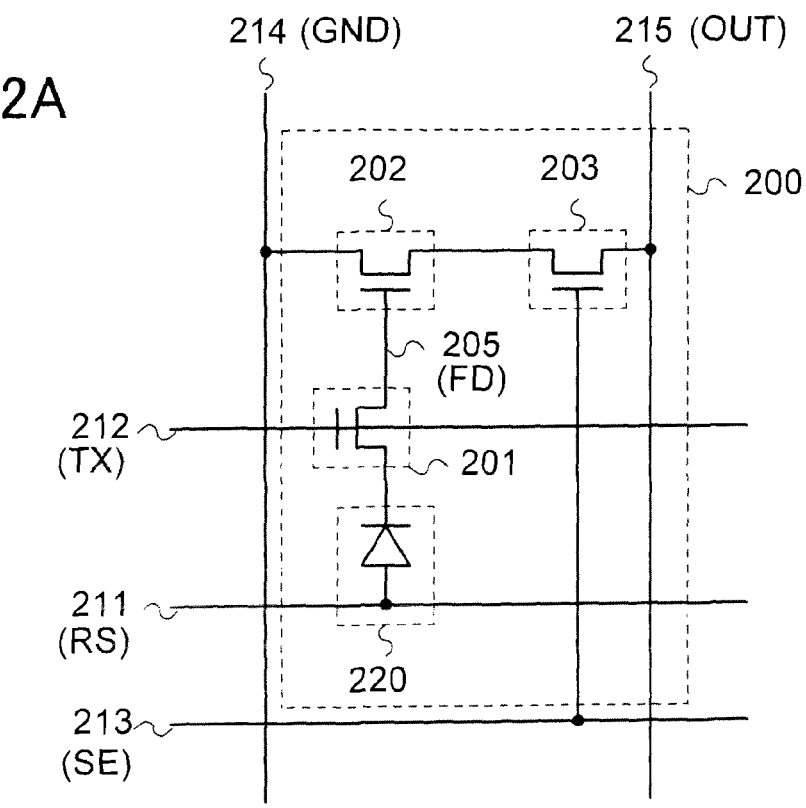
FIGS. 2A and 2B each illustrate a configuration of a pixel circuit.

The sensor substrate 101 includes a plurality of pixel circuits arranged in a matrix. An example of the pixel circuit is illustrated in FIG. 2A. A pixel circuit 200 includes a photodiode 220, a first transistor 201, a second transistor 202, and a third transistor 203, and functions as an optical sensor.

An anode of the photodiode 220 is electrically connected to a first wiring 211 (RS); a cathode of the photodiode 220 is electrically connected to one of a source and a drain of the first transistor 201; the other of the source and the drain of the first transistor 201 is electrically connected to a wiring 205 (FD); a gate of the first transistor 201 is electrically connected to a second wiring 212 (TX); one of a source and a drain of the second transistor 202 is electrically connected to a fourth wiring 214 (GND); the other of the source and the drain of the second transistor 202 is electrically connected to one of a source and a drain of the third transistor 203; a gate of the second transistor 202 is electrically connected to the wiring 205 (FD); the other of the source and the drain of the third transistor 203 is electrically connected to a fifth wiring 215 (OUT); and a gate of the third transistor 203 is electrically connected to a third wiring 213 (SE).

The photodiode 220 is an optical sensor element and generates current corresponding to the amount of light incident on the pixel circuit. The electrical charge generated by the photodiode 220 is accumulated in the wiring 205 (FD) by the first transistor 201. The second transistor 202 outputs a signal corresponding to a potential of the wiring 205 (FD). The third transistor 203 controls selection of the pixel circuits at the time of reading.

Note that the wiring 205 (FD) is a charge retention node, that is, a charge accumulation portion retaining an electrical charge whose amount changes depending on the amount of light received by the photodiode 220. Practically, the charge accumulation portion is depletion layer capacitance in the vicinity of a source region or a drain region of the first transistor 201 electrically connected to the wiring 205 (FD), wiring capacitance of the wiring 205 (FD), gate capacitance of the second transistor 202 electrically connected to the wiring 205 (FD), and the like.

The first wiring 211 (RS) is a signal line for resetting the wiring 205 (FD). The first wiring 211 (RS) in the pixel circuit 200 is also a signal line for performing charge accumulation in the wiring 205 (FD). The second wiring 212 (TX) is a signal line for controlling the first transistor 201. The third wiring 213 (SE) is a signal line for controlling the third transistor 203. The fourth wiring 214 (GND) is a signal line for setting a reference potential (e.g., GND). The fifth wiring 215 (OUT) is a signal line for reading data obtained in the pixel circuit 200.

Figure 2B:
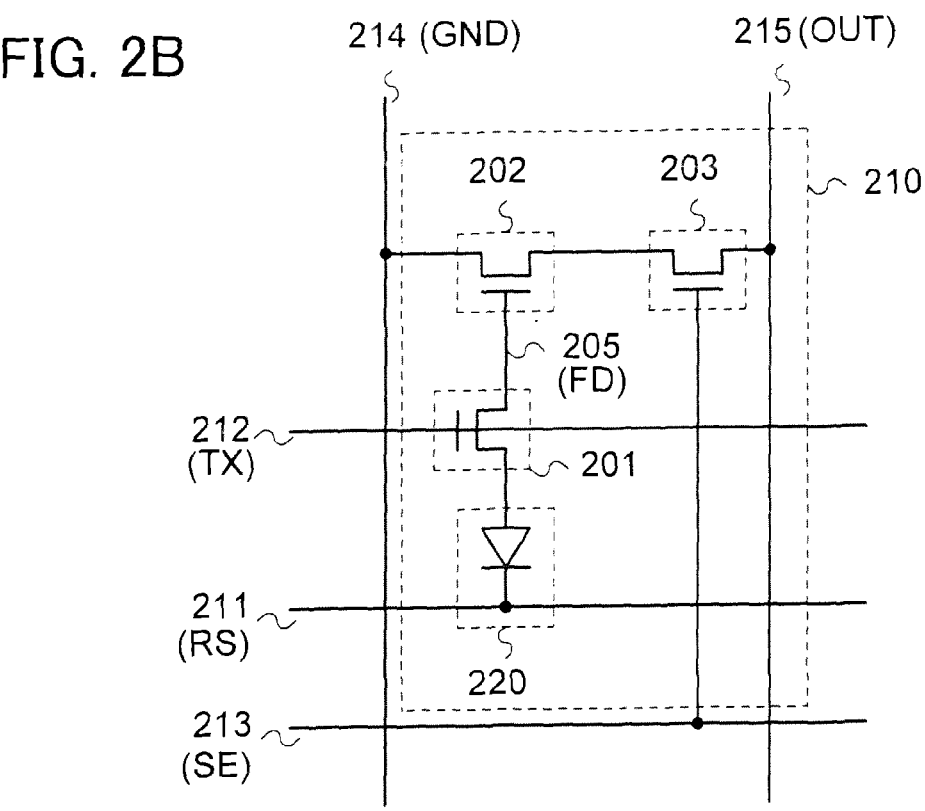

The pixel circuit may have a configuration illustrated in FIG. 2B. A pixel circuit 210 includes the same components as those in the pixel circuit 200 in FIG. 2A but is different from the pixel circuit 200 in that the anode of the photodiode 220 is electrically connected to one of the source and the drain of the first transistor 201 and the cathode of the photodiode 220 is electrically connected to the first wiring 211 (RS).

Figure 6A:
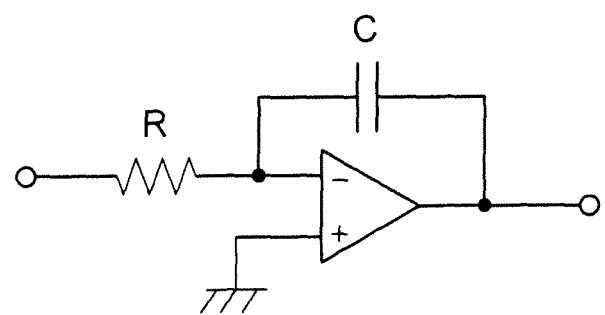
FIGS. 6A to 6C each illustrate an integrator circuit.
Figure 6B:
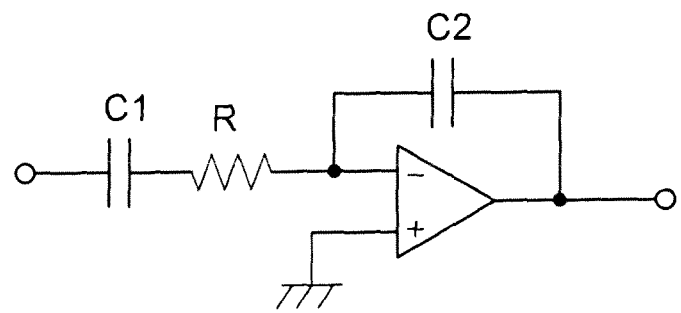
Figure 6C:
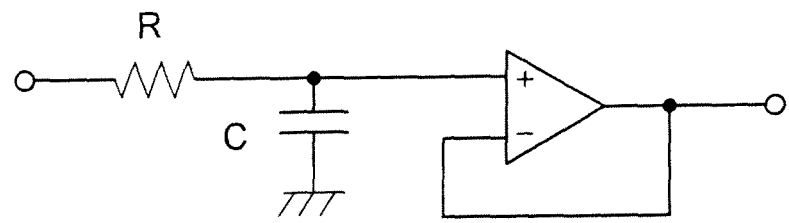

Note that the fifth wiring 215 (OUT) may be connected to an integrator circuit illustrated in FIG. 6A, 6B, or 6C. The circuit enables an S/N ratio of a reading signal to be increased, which makes it possible to sense weaker light, that is, to increase the sensitivity of the imaging device.

FIG. 6A illustrates an integrator circuit using an operational amplifier circuit (also referred to as an op-amp). An inverting input terminal of the operational amplifier circuit is connected to the fifth wiring 215 (OUT) through a resistor R. A non-inverting input terminal of the operational amplifier circuit is grounded. An output terminal of the operational amplifier circuit is connected to the inverting input terminal of the operational amplifier circuit through a capacitor C.

Here, the operational amplifier circuit is assumed to be an ideal operational amplifier circuit. In other words, it is assumed that input impedance is infinite (the input terminals draw no current). Since the potential of the non-inverting input terminal and the potential of the inverting input terminal are equal in a steady state, the potential of the inverting input terminal can be considered as a ground potential.

Equations (1) to (3) are satisfied, where Vi is the potential of the fifth wiring 215 (OUT), Vo is the potential of the output terminal of the operational amplifier circuit, i1 is a current flowing through the resistor R, and i2 is a current flowing through the capacitor C.

$$Vi = i1 \cdot R \tag{1}$$

$$i2 = C \cdot dVo/dt \tag{2}$$

$$i1 + i2 = 0 \tag{3}$$

Here, when electrical charge in the capacitor C is discharged at the time t=0, the potential Vo of the output terminal of the operational amplifier circuit at the time t=t is expressed by Equation (4).

$$Vo = -(1/CR)\int Vi\, dt \tag{4}$$

In other words, with a longer time t (integral time), the potential (Vi) to be read can be raised and output as the output signal Vo. Moreover, lengthening of the time t corresponds to averaging of thermal noise or the like and can increase an S/N ratio of the output signal Vo.

In a real operational amplifier circuit, a bias current flows even when a signal is not input to the input terminals, so that an output voltage is generated at the output terminal and electrical charge is accumulated in the capacitor C. It is therefore effective to connect a resistor in parallel with the capacitor C so that the capacitor C can be discharged.

FIG. 6B illustrates an integrator circuit including an operational amplifier circuit having a structure different from that in FIG. 6A. An inverting input terminal of the operational amplifier circuit is connected to the fifth wiring 215 (OUT) through a resistor R and a capacitor C1. A non-inverting input terminal of the operational amplifier circuit is grounded. An output terminal of the operational amplifier circuit is connected to the inverting input terminal of the operational amplifier circuit through a capacitor C2.

Here, the operational amplifier circuit is assumed to be an ideal operational amplifier circuit. In other words, it is assumed that input impedance is infinite (the input terminals draw no current). Since the potential of the non-inverting input terminal and the potential of the inverting input terminal are equal in a steady state, the potential of the inverting input terminal can be considered as a ground potential.

Equations (5) to (7) are satisfied, where Vi is the potential of the fifth wiring 215 (OUT), Vo is the potential of the output terminal of the operational amplifier circuit, i1 is a current flowing through the resistor R and the capacitor C1, and i2 is a current flowing through the capacitor C2.

$$Vi = (1/C1)\int i1\, dt + i1 \cdot R \tag{5}$$

$$i2 = C2 \cdot dVo/dt \tag{6}$$

$$i1 + i2 = 0 \tag{7}$$

Here, assuming that electrical charge in the capacitor C2 is discharged at the time t=0, as for the potential Vo of the output terminal of the operational amplifier circuit at the time t=t, Equation (9) corresponds to a high-frequency component when Inequality (8) is satisfied, and Equation (11) corresponds to a low-frequency component when Inequality (10) is satisfied.

$$VO << dVo/dt \tag{8}$$

$$Vo = -(1/C2R)\int Vi\, dt \tag{9}$$

$$Vo >> dVo/dt \tag{10}$$

$$Vo = -C1/C2 \cdot Vi \tag{11}$$

In other words, by appropriately setting the capacitance ratio of the capacitor C1 to the capacitor C2, the potential (Vi) to be read can be raised and output as the output signal Vo. Further, a high-frequency noise component of the input signal can be averaged by time integration, and an S/N ratio of the output signal Vo can be increased.

In a real operational amplifier circuit, a bias current flows even when a signal is not input to the input terminals, so that an output voltage is generated at the output terminal and electrical charge is accumulated in the capacitor C2. It is thus effective to connect a resistor in parallel with the capacitor C2 so that the capacitor C2 can be discharged.

FIG. 6C illustrates an integrator circuit using an operational amplifier circuit having a structure different from those in FIGS. 6A and 6B. A non-inverting input terminal of the operational amplifier circuit is connected to the fifth wiring 215 (OUT) through a resistor R and is grounded through a capacitor C. An output terminal of the operational amplifier circuit is connected to an inverting input terminal of the operational amplifier circuit. The resistor R and the capacitor C constitute a CR integrator circuit. The operational amplifier circuit is a unity gain buffer.

When Vi is the potential of the fifth wiring 215 (OUT) and Vo is the potential of the output terminal of the operational amplifier circuit, Vo can be expressed by Equation (12). Although Vo is saturated at the value of Vi, a noise component included in the input signal Vi can be averaged by the CR integrator circuit, and as a result, an S/N ratio of the output signal Vo can be increased.

$$Vo = (1/CR)\int Vi\, dt \tag{12}$$

Next, a structure of each element illustrated in FIGS. 2A and 2B is described.

The photodiode 220 can be formed using a silicon semiconductor with a pn junction or a pin junction, for example. Here, a pin photodiode including an i-type semiconductor layer formed of amorphous silicon is preferably used. Since amorphous silicon has optical absorption properties in a visible light wavelength region, visible light emitted from the scintillator 102 can be sensed.

Note that in this specification, an i-type semiconductor refers not only to what is called an intrinsic semiconductor in which the Fermi level lies in the middle of the band gap, but also to a semiconductor in which the concentration of an impurity imparting p-type conductivity and the concentration of an impurity imparting n-type conductivity are less than or equal to $1 \times 10^{20}$ atoms/cm$^3$ and in which the photoconductivity is higher than the dark conductivity.

Although a silicon semiconductor such as amorphous silicon, microcrystalline silicon, polycrystalline silicon, or single crystal silicon can be used to form the first transistor 201, the second transistor 202, and the third transistor 203, an oxide semiconductor is preferably used to form the first transistor 201, the second transistor 202, and the third transistor 203. A transistor in which a channel formation region is formed of an oxide semiconductor has an extremely small off-state current.

In particular, when the first transistor 201 connected to the wiring 205 (FD) has a large leakage current, electrical charges accumulated in the wiring 205 (FD) cannot be retained for a sufficiently long time; thus, at least the first transistor 201 is preferably formed using an oxide semiconductor. The use of the transistor using an oxide semiconductor can prevent unwanted output of electrical charges through the photodiode.

Unwanted output of electrical charges also occurs in the fourth wiring 214 or the fifth wiring 215 when the second transistor 202 and the third transistor 203 have a large leakage current; thus, a transistor in which a channel formation region is formed of an oxide semiconductor is preferably used as these transistors.

When the transistor using an oxide semiconductor and having an extremely small off-state current is used as the second transistor 202, imaging can be performed with higher dynamic range. In the pixel circuit illustrated in FIG. 2A, a gate potential of the second transistor 202 is decreased when the intensity of light incident on the photodiode is increased. In the pixel circuit illustrated in FIG. 2B, the gate potential of the second transistor 202 is decreased when the intensity of light incident on the photodiode is decreased. Since the transistor using an oxide semiconductor has an extremely small off-state current, a current corresponding to the gate potential can be accurately output even when the gate potential is extremely low. Thus, it is possible to broaden the detection range of illuminance, i.e., the dynamic range.

Further, in the pixel circuit illustrated in FIG. 2B, sufficiently high dynamic range can be obtained even when the gate potential of the second transistor 202 is relatively low, i.e., when the intensity of light emitted from the scintillator to the photodiode is low. In other words, the scintillator does not need to emit high-intensity light, which makes it possible to reduce the intensity of X-rays emitted to an object.

Next, an example of the operation of the pixel circuit 200 in FIG. 2A is described with reference to a timing chart in FIG. 3A.

In FIG. 3A, a potential of each wiring is denoted as a signal which varies between two levels for simplicity. Note that in practice, the potential can have various levels depending on circumstances without limitation on two levels because each potential is an analog signal. In the drawing, a signal 301 corresponds to a potential of the first wiring 211 (RS); a signal 302, a potential of the second wiring 212 (TX); a signal 303, a potential of the third wiring 213 (SE); a signal 304, a potential of the wiring 205 (FD); and a signal 305, a potential of the fifth wiring 215 (OUT).

At time A, the potential of the first wiring 211 (signal 301) is set high and the potential of the second wiring 212 (signal 302) is set high, whereby a forward bias is applied to the photodiode 220 and the potential of the wiring 205 (signal 304) is set high. In other words, the potential of the charge accumulation portion is initialized to the potential of the first wiring 211 and brought into a reset state. The above is the start of a reset operation. Note that the potential of the fifth wiring 215 (signal 305) is precharged to high level.

At time B, the potential of the first wiring 211 (signal 301) is set low and the potential of the second wiring 212 (signal 302) is set high, so that the reset operation is terminated and an accumulation operation is started. Here, a reverse bias is applied to the photodiode 220, whereby the potential of the wiring 205 (signal 304) is started to decrease due to a reverse current. Since the reverse current is increased when the photodiode 220 is irradiated with light, the rate of decrease in the potential of the wiring 205 (signal 304) changes depending on the amount of the light irradiation. In other words, channel resistance between the source and the drain of the second transistor 202 changes depending on the amount of light emitted to the photodiode 220.

Note that the light emitted to the photodiode 220 refers to the visible light 105 which is converted from the X-ray 104 by the scintillator 102.

At time C, the potential of the second wiring 212 (signal 302) is set low to terminate the accumulation operation, so that the potential of the wiring 205 (signal 304) becomes constant. Here, the potential is determined by the amount of electrical charge generated by the photodiode 220 during the accumulation operation. That is, the potential changes depending on the amount of light emitted to the photodiode 220. Further, since the first transistor 201 is a transistor which includes a channel formation region formed of an oxide semiconductor layer and which has an extremely small off-state current, the potential of the wiring 205 can be kept constant until a subsequent selection operation (read operation) is terminated.

Note that in some cases, the potential of the wiring 205 changes due to parasitic capacitance between the second wiring 212 and the wiring 205 when the potential of the second wiring 212 (signal 302) is set low. In the case where the potential changes significantly, the amount of electrical charge generated by the photodiode 220 during the accumulation operation cannot be obtained accurately. Examples of effective measures to reduce the amount of change in the potential include reducing the capacitance between the gate and the source (or between the gate and the drain) of the first transistor 201, increasing the gate capacitance of the second transistor 202, and providing a storage capacitor to connect the wiring 205. Note that in this embodiment, the change in the potential can be ignored by the adoption of these measures.

At time D, the potential of the third wiring 213 (signal 303) is set high to turn on the third transistor 203, whereby the selection operation is started and the fourth wiring 214 and the fifth wiring 215 are electrically connected to each other through the second transistor 202 and the third transistor 203. Also, the potential of the fifth wiring 215 (signal 305) is started to decrease. Note that precharge of the fifth wiring 215 only needs to be terminated before time D. Here, the rate of decrease in the potential of the fifth wiring 215 (signal 305) depends on the current between the source and the drain of the second transistor 202. That is, the potential changes depending on the amount of light emitted to the photodiode 220 during the accumulation operation.

At time E, the potential of the third wiring 213 (signal 303) is set low to turn off the third transistor 203, so that the selection operation is terminated and the potential of the fifth wiring 215 (signal 305) becomes a constant value. Here, the constant value changes depending on the amount of light emitted to the photodiode 220. Therefore, the amount of light emitted to the photodiode 220 during the accumulation operation can be known by obtaining the potential of the fifth wiring 215.

Specifically, the stronger the light emitted to the photodiode 220 is, the lower the potential of the wiring 205 is and the lower a gate voltage of the second transistor 202 is, resulting in a gradual decrease in the potential of the fifth wiring 215 (signal 1Q 305). Thus, a relatively high potential can be read from the fifth wiring 215.

Conversely, the weaker the light emitted to the photodiode 220 is, the higher the potential of the wiring 205 is and the higher the gate voltage of the second transistor 202 is, resulting in a rapid decrease in the potential of the fifth wiring 215 (signal 305). Thus, a relatively low potential can be read from the fifth wiring 215.

Next, an example of the operation of the pixel circuit 210 in FIG. 2B is described with reference to a timing chart in FIG. 3B.

At time A, the potential of the first wiring 211 (signal 301) is set low and the potential of the second wiring 212 (signal 302) is set high, whereby a forward bias is applied to the photodiode 220 and the potential of the wiring 205 (signal 304) is set low. In other words, the potential of the charge accumulation portion is brought into a reset state. The above is the start of a reset operation. Note that the potential of the fifth wiring 215 (signal 305) is precharged to high level.

At time B, the potential of the first wiring 211 (signal 301) is set high and the potential of the second wiring 212 (signal 302) is set high, so that the reset operation is terminated and an accumulation operation is started. Here, a reverse bias is applied to the photodiode 220, whereby the potential of the wiring 205 (signal 304) is started to increase due to a reverse current. Since the reverse current is increased when the photodiode 220 is irradiated with light, the rate of increase in the potential of the wiring 205 (signal 304) changes depending on the amount of the light irradiation. In other words, channel resistance between the source and the drain of the second transistor 202 changes depending on the amount of light emitted to the photodiode 220.

Operations after time C are the same as those of the timing chart in FIG. 3A. The amount of light emitted to the photodiode 220 during the accumulation operation can be known by obtaining the potential of the fifth wiring 215 at time E.

Figure 4A:
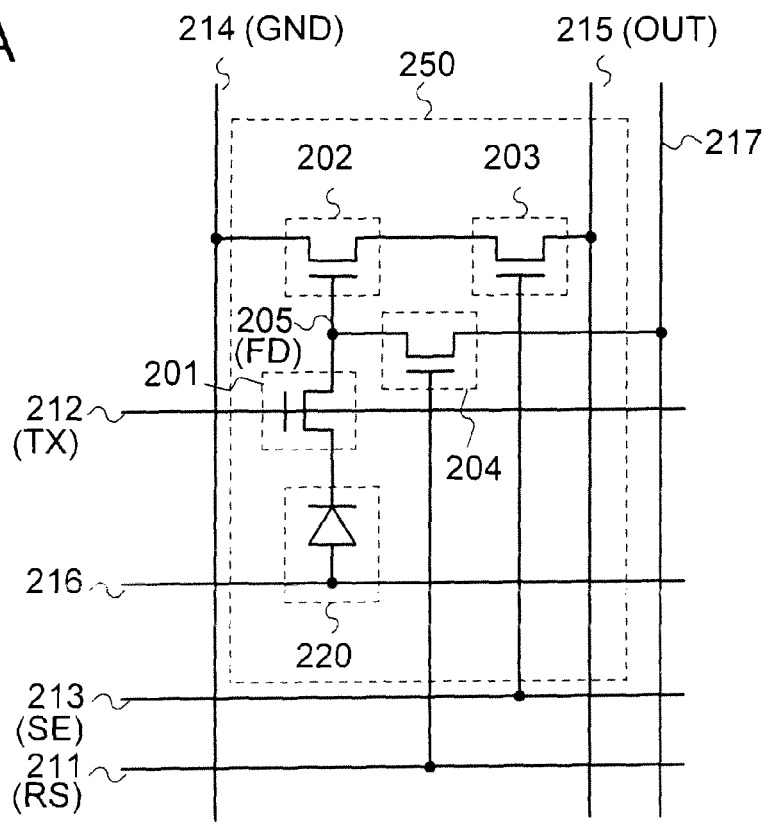
FIGS. 4A and 4B each illustrate a configuration of a pixel circuit.
Figure 4B:
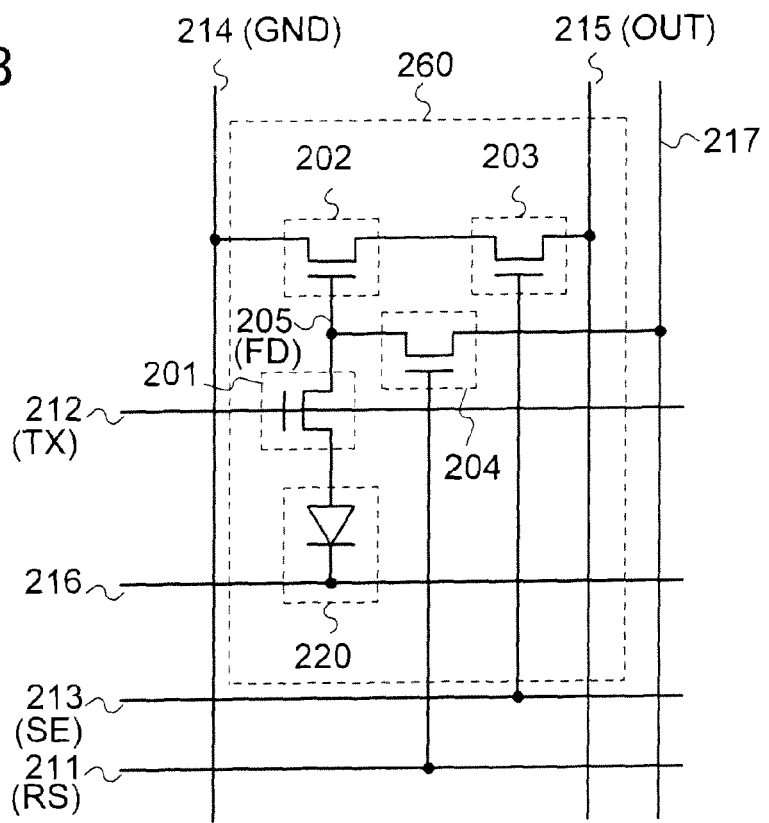

Further, the pixel circuit included in the sensor substrate 101 of one embodiment of the present invention may have a configuration illustrated in FIG. 4A or FIG. 4B.

A pixel circuit 250 illustrated in FIG. 4A has a configuration in which a fourth transistor 204 is added to the pixel circuit 200 in FIG. 2A. A gate of the transistor is electrically connected to the first wiring 211 (RS); one of a source and a drain of the transistor, the wiring 205 (FD); the other of the source and the drain of the transistor, a seventh wiring 217; and the anode of the photodiode 220, a sixth wiring 216. Here, the sixth wiring 216 is a signal line (low potential line) for applying a reverse bias to the photodiode 220 all the time. The seventh wiring 217 is a signal line (high potential line) for resetting the wiring 205 so that the wiring 205 has a high potential.

The fourth transistor 204 serves as a reset transistor for resetting the wiring 205 (FD). Hence, unlike in the pixel circuit 200 in FIG. 2A, the reset operation using the photodiode 220 is not performed and a reverse bias is applied to the photodiode all the time. The wiring 205 (FD) can be reset by setting the potential of the first wiring 211 (RS) high. Operations of the pixel circuit 250 are the same as those of the pixel circuit 200 in FIG. 2A, which are illustrated in the timing chart in FIG. 3A.

A pixel circuit 260 illustrated in FIG. 4B has a configuration in which the fourth transistor 204 is added to the pixel circuit 210 in FIG. 2B. The gate of the transistor is electrically connected to the first wiring 211 (RS); one of the source and the drain of the transistor, the wiring 205 (FD); the other of the source and the drain of the transistor, the seventh wiring 217; and the cathode of the photodiode 220, the sixth wiring 216. Here, the sixth wiring 216 is a signal line (high potential line) for applying a reverse bias to the photodiode 220 all the time. The seventh wiring 217 is a signal line (low potential line) for resetting the wiring 205 so that the wiring 205 has a low potential.

The fourth transistor 204 serves as a reset transistor for resetting the wiring 205 (FD). Hence, unlike in the pixel circuit 210 in FIG. 2B, the reset operation using the photodiode 220 is not performed and a reverse bias is applied to the photodiode all the time. The wiring 205 (FD) can be reset by setting the potential of the first wiring 211 (RS) high. The pixel circuit 260 can operate in accordance with a timing chart in FIG. 3C.

The fourth transistor 204 can be formed using a silicon semiconductor such as amorphous silicon, microcrystalline silicon, polycrystalline silicon, or single crystal silicon; however, when the fourth transistor 204 has a large leakage current, electrical charges cannot be retained in the charge accumulation portion for a sufficiently long time. For this reason, a transistor formed using an oxide semiconductor and having an extremely small off-state current is preferably used as the fourth transistor 204, as in the case of the first transistor 201.

Figure 5:
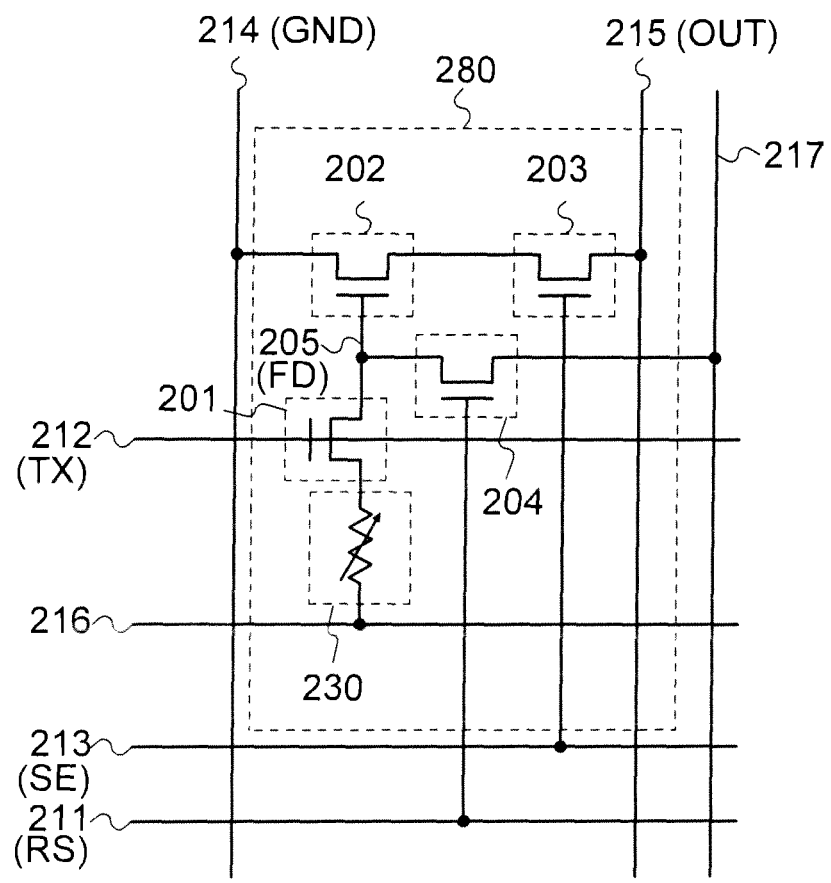
FIG. 5 illustrates a configuration of a pixel circuit.

Further, the pixel circuit included in the sensor substrate 101 of one embodiment of the present invention may have a configuration illustrated in FIG. 5. A pixel circuit 280 in FIG. 5 has the same configuration as that in FIG. 4A or FIG. 4B except that as an optical sensor element, a variable resistor 230 is used instead of the photodiode. The variable resistor can have a structure including a pair of electrodes and an i-type amorphous silicon layer provided between the pair of electrodes. Since the resistance of the i-type amorphous silicon layer changes due to light irradiation, the potential of the wiring 205 can be changed as in the case of using the photodiode, which enables the amount of light emitted to the variable resistor 230 during the accumulation operation to be known.

By setting the potential of the sixth wiring 216 low and the seventh wiring 217 high, the pixel circuit 280 in FIG. 5 can operate in accordance with the timing chart in FIG. 3A. Further, by setting the potential of the sixth wiring 216 high and the seventh wiring 217 low, the pixel circuit 280 can operate in accordance with the timing chart in FIG. 3C.

As described above, the operation of each pixel circuit in the imaging device is repetition of the reset operation, the accumulation operation, and the selection operation. To achieve imaging of the imaging device in short time, it is necessary to perform the reset operation, the accumulation operation, and the selection operation of all the pixel circuits at high speed.

Figure 7A:
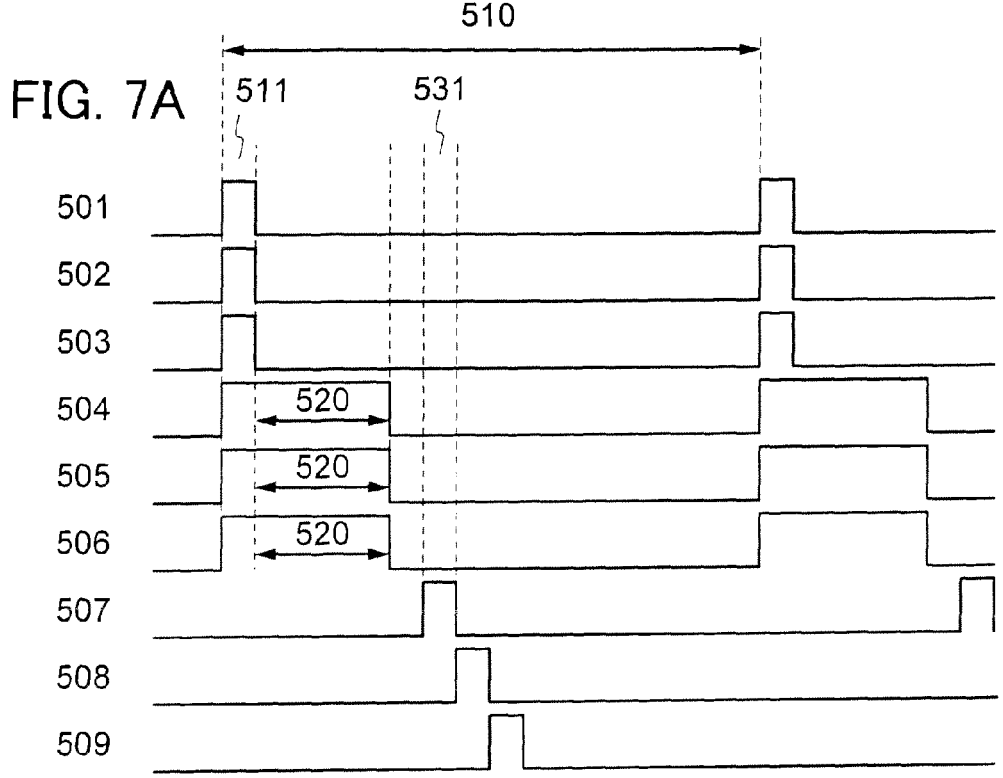
FIGS. 7A and 7B are timing charts illustrating the operations in a global shutter system and a rolling shutter system, respectively.

Thus, a driving method using a global shutter system illustrated in a timing chart in FIG. 7A is used for imaging in one embodiment of the present invention. Note that FIG. 7A shows operations of the pixel circuits 200 in FIG. 2A from the first row to the third row in the sensor substrate 101.

In FIG. 7A, a signal 501, a signal 502, and a signal 503 are signals input to the first wiring 211 (RS) connected to the pixel circuits in the first row, the second row, and the third row, respectively. A signal 504, a signal 505, and a signal 506 are signals input to the second wiring 212 (TX) connected to the pixel circuits in the first row, the second row, and the third row, respectively. A signal 507, a signal 508, and a signal 509 are signals input to the third wiring 213 (SE) connected to the pixel circuits in the first row, the second row, and the third row, respectively.

A period 510 is a period required for one imaging. In a period 511, the reset operation is performed in the pixel circuits in each row. In a period 520, the accumulation operation is performed in the pixel circuits in each row. Note that the selection operation is sequentially performed in the pixel circuits for each row. For example, in a period 531, the selection operation is performed in the pixel circuits in the first row. As described above, in the global shutter system, the reset operation is performed in all the pixel circuits substantially at the same time, the accumulation operation is performed in all the pixel circuits substantially at the same time, and then the read operation is sequentially performed for each row.

That is, in the global shutter system, since the accumulation operation is performed in all the pixel circuits substantially at the same time, imaging is simultaneously performed in the pixel circuits in all the rows. Thus, X-ray irradiation in synchronization with the accumulation operation can shorten the time of the X-ray irradiation to an object. That is, the X-ray irradiation is performed only in the period 520.

Figure 7B:
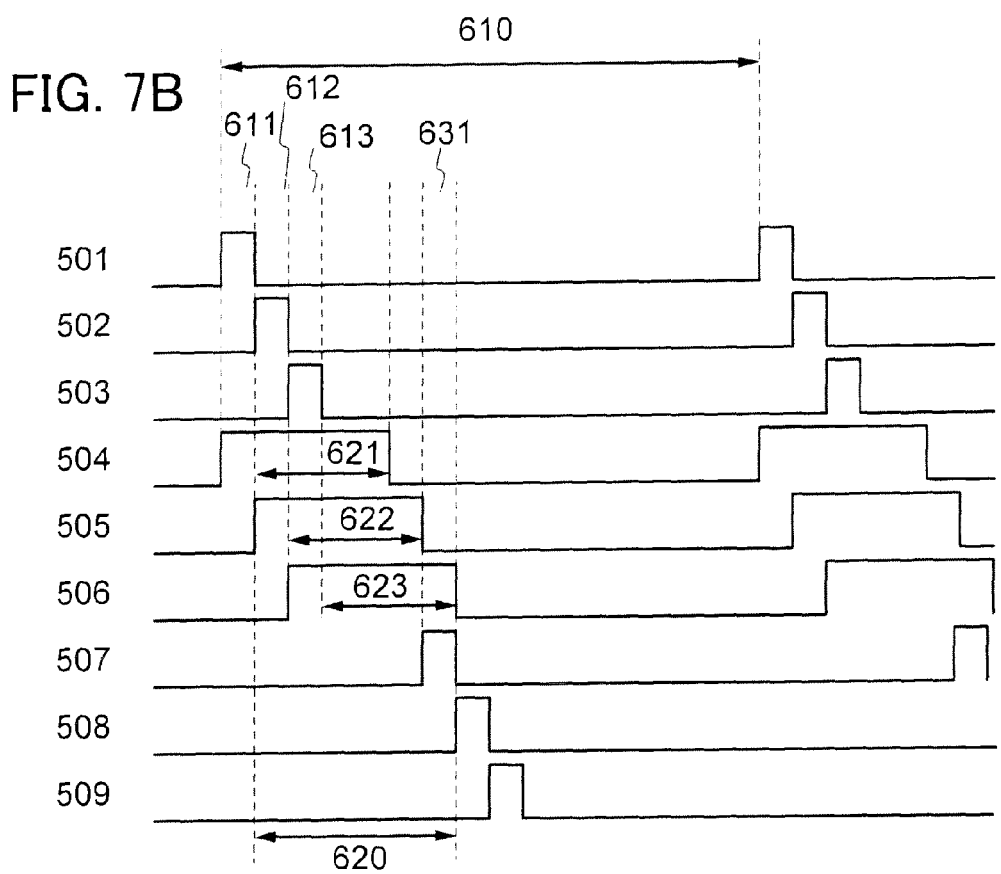

On the other hand, FIG. 7B is a timing chart of the case where a rolling shutter system is used. A period 610 is a period required for one imaging. A period 611, a period 612, and a period 612 are reset periods in the first row, the second row, and the third row, respectively. A period 621, a period 622, and a period 623 are accumulation operation periods in the first row, the second row, and the third row, respectively. In a period 631, the selection operation is performed in the pixel circuits in the first row. As described above, in the rolling shutter system, the accumulation operation is not performed at the same time in all the pixel circuits but is sequentially performed for each row; thus, imaging is not simultaneously performed in the pixel circuits in all the rows. For this reason, even when the X-ray irradiation is synchronized with the accumulation operation, an X-ray irradiation period 620 is longer than that in the global shutter system.

To realize the global shutter system, even after the accumulation operation, the potential of the wiring 205 (FD) in each pixel circuit needs to be kept for a long time until the read operation is terminated. As described above, when a transistor including a channel formation region formed of an oxide semiconductor and having an extremely small off-state current is used as the first transistor 201, the potential of the wiring 205 (FD) can be kept for a long time. On the other hand, in the case where a transistor including a channel formation region formed of a silicon semiconductor or the like is used as the first transistor 201, the potential of the wiring 205 (FD) cannot be kept for a long time because of a large off-state current, which makes it difficult to use the global shutter system; thus, the rolling shutter system has to be used.

As described above, the use of the transistor including a channel formation region formed of an oxide semiconductor in the pixel circuits makes it easy to realize the global shutter system, and thus the imaging device with a small amount of X-rays emitted to an object can be provided.

This embodiment can be freely combined with any of the other embodiments in this specification.

(Embodiment 2)

In this embodiment, detailed description is given of a configuration of the sensor substrate 101 described in Embodiment 1. Examples of the configuration of the sensor substrate 101 including pixel circuits arranged in a matrix with m rows and n columns are described with reference to FIGS. 8 to 11.

Figure 8:
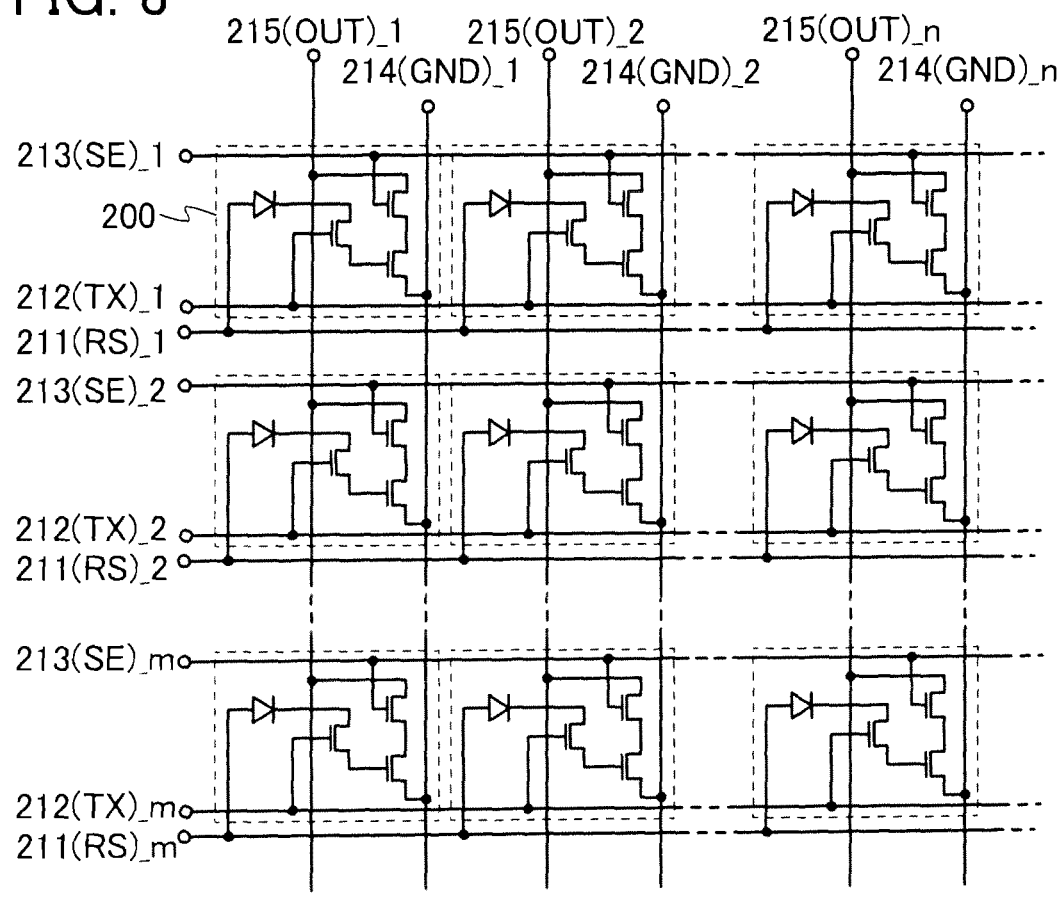
FIG. 8 is a circuit diagram of a plurality of pixel circuits arranged in a matrix.

FIG. 8 is an example of arranging a plurality of pixel circuits 200 illustrated in FIG. 2A in a matrix with m (m is a natural number of two or more) rows and n (n is a natural number of two or more) columns. Each of the pixel circuits 200 is electrically connected to any one of a plurality of first wirings 211 (RS) (211(RS)_1 to 211(RS)_m), any one of a plurality of second wirings 212 (TX) (212(TX)_1 to 212 (TX)_m), any one of a plurality of third wirings 213 (SE) (213(SE)_1 to 213(SE)_m), any one of a plurality of fourth wirings 214 (GND) (214(GND)_1 to 214(GND)_n), and any one of a plurality of fifth wirings 215 (OUT) (215(OUT)_1 to 215(OUT)_n).

In FIG. 8, the pixel circuits 200 in each row (a horizontal direction in the drawing) share the first wiring 211 (RS), the second wiring 212 (TX), and the third wiring 213 (SE). The pixel circuits 200 in each column (a vertical direction in the drawing) share the fourth wiring 214 (GND) and the fifth wiring 215 (OUT). However, one embodiment of the present invention is not limited to this configuration. A plurality of first wirings 211 (RS), a plurality of second wirings 212 (TX), and a plurality of third wirings 213 (SE) may be provided in each row to be electrically connected to the respective pixel circuits 200. A plurality of fourth wirings 214 (GND) and a plurality of fifth wirings 215 (OUT) may be provided in each column to be electrically connected to the respective pixel circuits 200.

Although the fourth wiring 214 (GND) is shared by the pixel circuits 200 in each column in FIG. 8, the fourth wiring 214 (GND) may be shared by the pixel circuits 200 in each row.

As described above, wirings are shared to reduce the number of wirings, so that a driver circuit for driving the pixel circuits 200 arranged in a matrix with m rows and n columns can be simplified.

Figure 9:
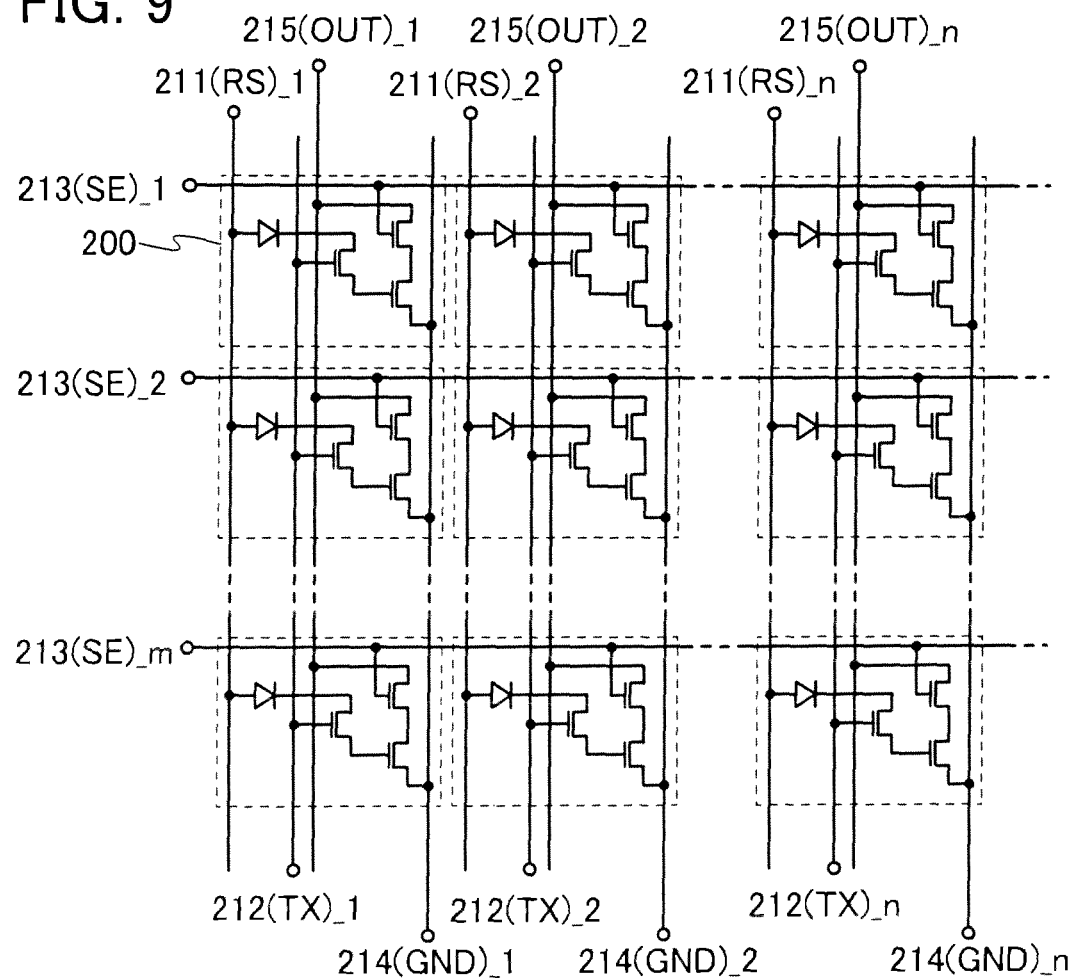
FIG. 9 is a circuit diagram of a plurality of pixel circuits arranged in a matrix.

In FIG. 9, the plurality of pixel circuits 200 is arranged in a matrix with m rows and n columns. Each of the pixel circuits 200 is electrically connected to any one of the plurality of first wirings 211 (RS) (211(RS)_1 to 211(RS)_n), any one of the plurality of second wirings 212 (TX) (212(TX)_1 to 212(TX)_n), any one of the plurality of third wirings 213 (SE) (213(SE)_1 to 213(SE)_m), any one of the plurality of fourth wirings 214 (GND) (214(GND)_1 to 214(GND)_n), and any one of the plurality of fifth wirings 215 (OUT) (215(OUT)_1 to 215(OUT)_n).

In FIG. 9, the pixel circuits 200 in each row share the third wiring 213 (SE). The pixel circuits 200 in each column share the first wiring 211 (RS), the second wiring 212 (TX), the fourth wiring 214 (GND), and the fifth wiring 215 (OUT). However, one embodiment of the present invention is not limited to this configuration. A plurality of third wirings 213

(SE) may be provided in each row to be electrically connected to the respective pixel circuits 200. A plurality of first wirings 211 (RS), a plurality of second wirings 212 (TX), a plurality of fourth wirings 214 (GND), and a plurality of fifth wirings 215 (OUT) may be provided in each column to be electrically connected to the respective pixel circuits 200.

Although the fourth wiring 214 (GND) is shared by the pixel circuits 200 in each column in FIG. 9, the fourth wiring 214 (GND) may be shared by the pixel circuits 200 in each row.

As described above, wirings are shared to reduce the number of wirings, so that a driver circuit for driving the pixel circuits 200 arranged in a matrix with m rows and n columns can be simplified.

Note that in the configurations in FIGS. 8 and 9, the pixel circuit 210 illustrated in FIG. 2B can be substituted for the pixel circuit 200.

Figure 10:
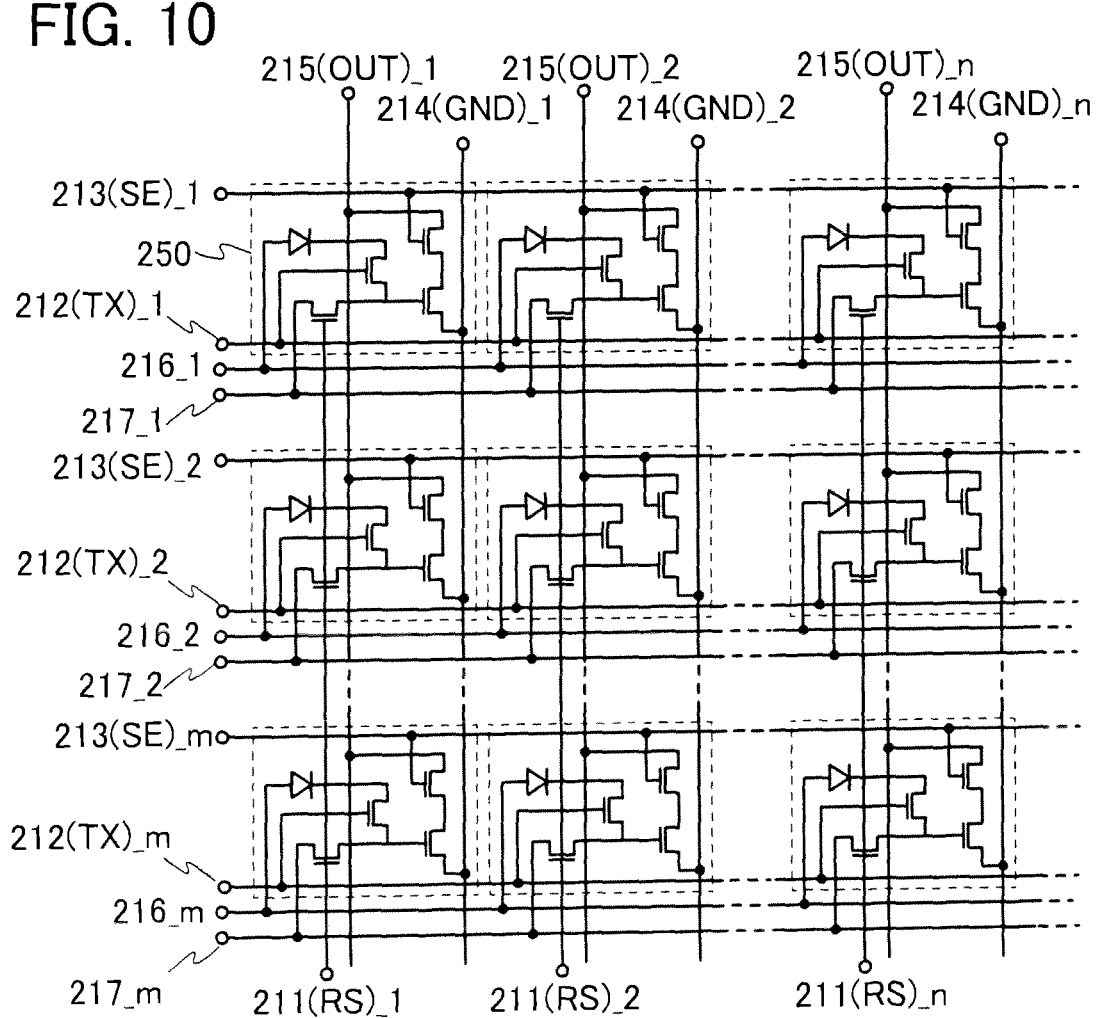
FIG. 10 is a circuit diagram of a plurality of pixel circuits arranged in a matrix.

FIG. 10 is an example of arranging a plurality of pixel circuits 250 illustrated in FIG. 4A in a matrix with m rows and n columns. Each of the pixel circuits 250 is connected to any one of the plurality of first wirings 211 (RS) (211(RS)_1 to 211(RS)_n), any one of the plurality of second wirings 212 (TX) (212(TX)_1 to 212(TX)_m), any one of the plurality of third wirings 213 (SE) (213(SE)_1 to 213(SE)_m), any one of the plurality of fourth wirings 214 (GND) (214(GND)_1 to 214(GND)_n), any one of the plurality of fifth wirings 215 (OUT) (215(OUT)_1 to 215(OUT)_n), any one of a plurality of sixth wirings 216 (216_1 to 216_m), and any one of a plurality of seventh wirings 217 (217_1 to 217_m).

In FIG. 10, the pixel circuits 250 in each row (a horizontal direction in the drawing) share the second wiring 212 (TX), the third wiring 213 (SE), and the sixth wiring 216. The pixel circuits 250 in each column (a vertical direction in the drawing) share the first wiring 211 (RS), the fourth wiring 214 (GND), and the fifth wiring 215 (OUT). However, one embodiment of the present invention is not limited to this configuration. A plurality of second wirings 212 (TX), a plurality of third wirings 213 (SE), and a plurality of sixth wirings 216 may be provided in each row to be electrically connected to the respective pixel circuits 250. A plurality of first wirings 211 (RS), a plurality of fourth wirings 214 (GND), and a plurality of fifth wirings 215 (OUT) may be provided in each column to be electrically connected to the respective pixel circuits 250.

Although the first wiring 211 (RS) is shared by the pixel circuits 250 in each column in FIG. 10, the first wiring 211 (RS) may be shared by the pixel circuits 250 in each row.

Although the fourth wiring 214 (GND) is shared by the pixel circuits 250 in each column in FIG. 10, the fourth wiring 214 (GND) may be shared by the pixel circuits 250 in each row.

Although the seventh wiring 217 is shared by the pixel circuits 250 in each row in FIG. 10, the seventh wiring 217 may be shared by the pixel circuits 250 in each column.

As described above, wirings are shared to reduce the number of wirings, so that a driver circuit for driving the pixel circuits 250 arranged in a matrix with m rows and n columns can be simplified.

Figure 11:
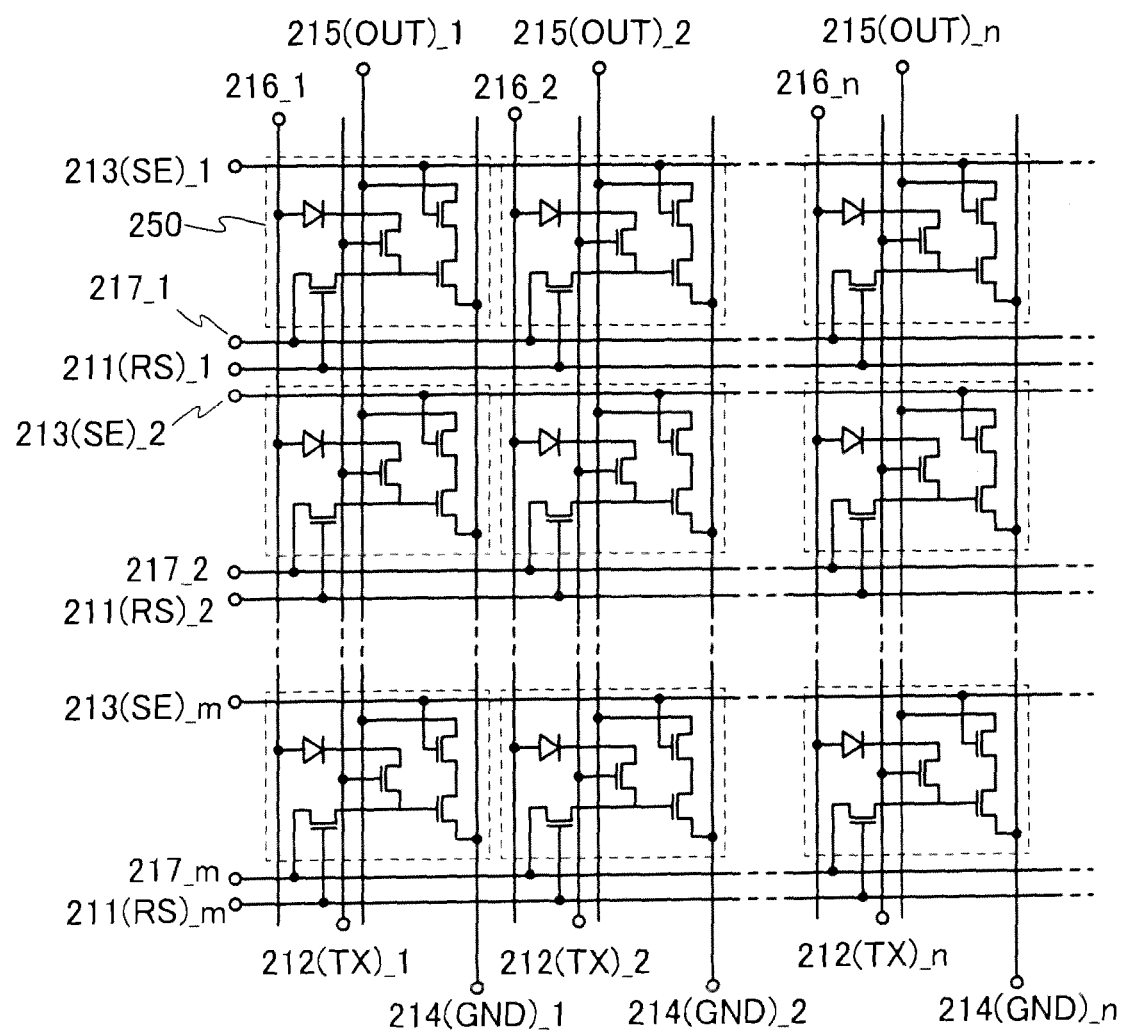
FIG. 11 is a circuit diagram of a plurality of pixel circuits arranged in a matrix.

FIG. 11 is an example of arranging a plurality of pixel circuits 250 in a matrix with in rows and n columns. Each of the pixel circuits 250 is connected to any one of the plurality of first wirings 211 (RS) (211(RS)_1 to 211(RS)_m), any one of the plurality of second wirings 212 (TX) (212(TX)_1 to 212(TX)_n), any one of the plurality of third wirings 213 (SE) (213(SE)_1 to 213(SE)_m), any one of the plurality of fourth wirings 214 (GND) (214(GND)_1 to 214(GND)_n), any one of the plurality of fifth wirings 215 (OUT) (215(OUT)_1 to 215(OUT)_n), any one of a plurality of sixth wirings 216 (216_1 to 216_n), and any one of a plurality of seventh wirings 217 (217_1 to 217_m).

In FIG. 11, the pixel circuits 250 in each row (a horizontal direction in the drawing) share the first wiring 211 (RS), the third wiring 213 (SE), and the seventh wiring 217. The pixel circuits 250 in each column (a vertical direction in the drawing) share the second wiring 212 (TX), the fourth wiring 214 (GND), the fifth wiring 215 (OUT), and the sixth wiring 216. However, one embodiment of the present invention is not limited to this configuration. A plurality of first wirings 211 (RS), a plurality of third wirings 213 (SE), and a plurality of seventh wirings 217 may be provided in each row to be electrically connected to the respective pixel circuits 250. A plurality of second wirings 212 (TX), a plurality of fourth wirings 214 (GND), a plurality of fifth wirings 215 (OUT), and a plurality of sixth wirings 216 may be provided in each column to be electrically connected to the respective pixel circuits 250.

Although the first wiring 211 (RS) is shared by the pixel circuits 250 in each row in FIG. 11, the first wiring 211 (RS) may be shared by the pixel circuits 250 in each column.

Although the fourth wiring 214 (GND) is shared by the pixel circuits 250 in each column in FIG. 11, the fourth wiring 214 (GND) may be shared by the pixel circuits 250 in each row.

Although the seventh wiring 217 is shared by the pixel circuits 250 in each row in FIG. 11, the seventh wiring 217 may be shared by the pixel circuits 250 in each column.

As described above, wirings are shared to reduce the number of wirings, so that a driver circuit for driving the pixel circuits 250 arranged in a matrix with m rows and n columns can be simplified.

Note that in the configurations in FIGS. 10 and 11, the pixel circuit 260 illustrated in FIG. 4B or the pixel circuit 280 illustrated in FIG. 5 can be substituted for the pixel circuit 250.

Next, an example of a layout of the pixel circuit 200 illustrated in FIG. 2A is described with reference to FIGS. 12A and 12B.

Figure 12A:
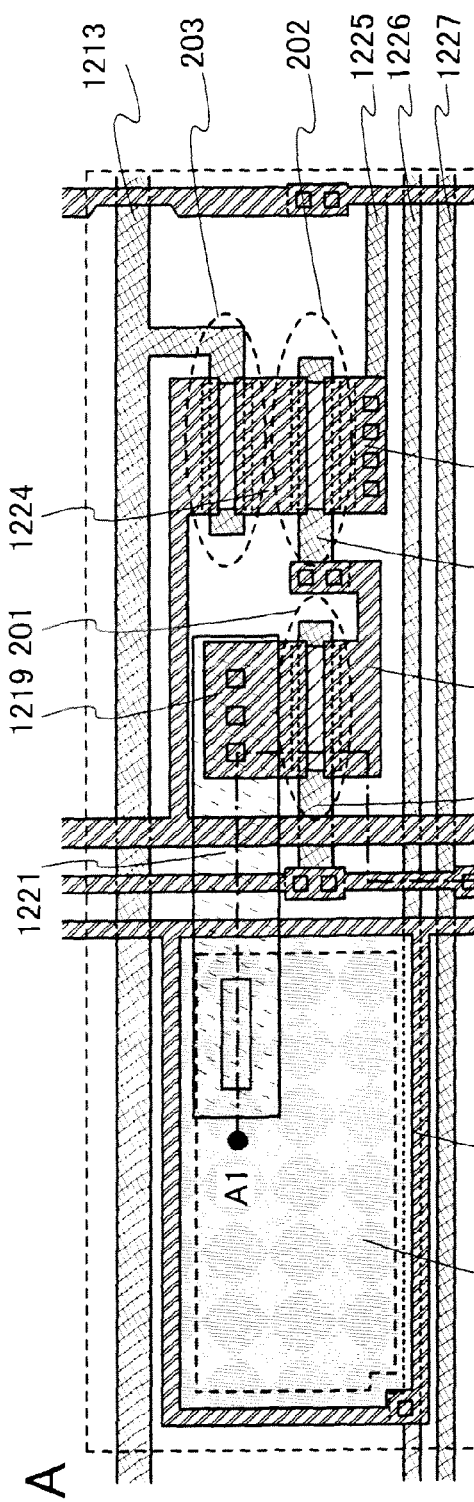
FIGS. 12A and 12B are respectively a top view and a cross-sectional view of a layout of a pixel circuit.
Figure 12B:
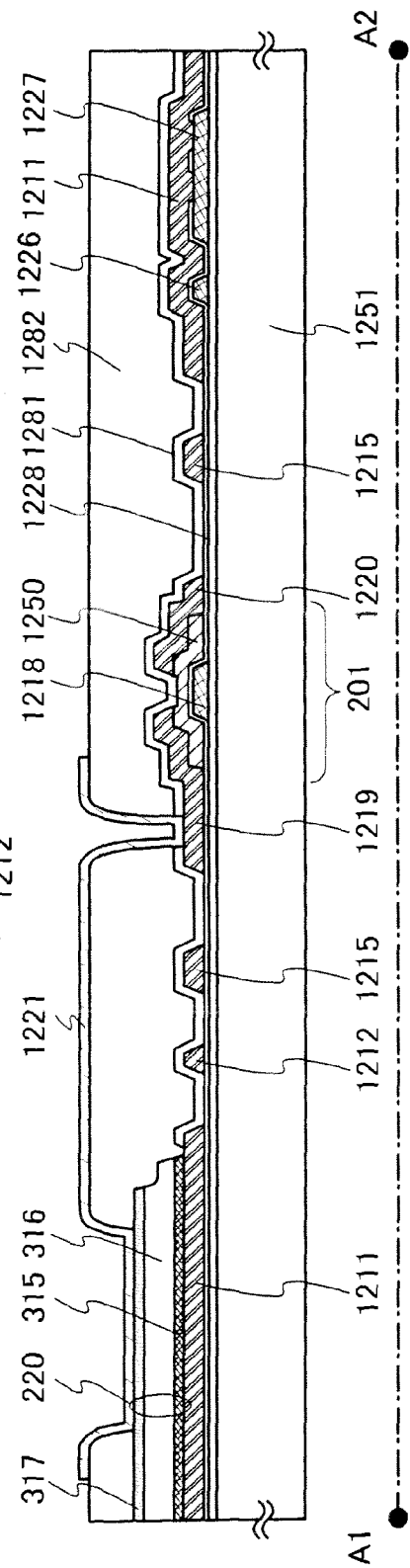

FIG. 12A is a top view of the pixel circuit 200 and FIG. 12B is a cross-sectional view taken along the dashed line A1-A2 in FIG. 12A.

The pixel circuit 200 includes a conductive film 1211 serving as the first wiring 211 (RS), a conductive film 1212 serving as the second wiring 212 (TX), a conductive film 1213 serving as the third wiring 213 (SE), a conductive film 1214 serving as the fourth wiring 214 (GND), and a conductive film 1215 serving as the fifth wiring 215 (OUT).

The photodiode 220 included in the pixel circuit 200 includes a p-type semiconductor film 315, an i-type semiconductor film 316, and an n-type semiconductor film 317 which are stacked in this order. The conductive film 1211 is electrically connected to the p-type semiconductor film 315 serving as the anode of the photodiode 220.

A conductive film 1218 included in the pixel circuit 200 serves as a gate electrode of the first transistor 201 and is electrically connected to the conductive film 1212. A conductive film 1219 included in the pixel circuit 200 serves as one of a source electrode and a drain electrode of the first transistor 201. A conductive film 1220 included in the pixel circuit 200 serves as the other of the source electrode and the drain electrode of the first transistor 201. A conductive film 1221 included in the pixel circuit 200 is electrically connected to the n-type semiconductor film 317 and the conductive film 1219. A conductive film 1222 included in the pixel circuit 200 serves as a gate electrode of the second transistor 202 and is electrically connected to the conductive film 1220.

A conductive film 1223 included in the pixel circuit 200 serves as one of a source electrode and a drain electrode of the second transistor 202. A conductive film 1224 included in the pixel circuit 200 serves as the other of the source electrode and the drain electrode of the second transistor 202 and one of a source electrode and a drain electrode of the third transistor 203. The conductive film 1214 serves as the other of the source electrode and the drain electrode of the third transistor 203. The conductive film 1213 also serves as a gate electrode of the third transistor 203. A conductive film 1225 included in the pixel circuit 200 is electrically connected to the conductive film 1223 and the conductive film 1214.

In FIGS. 12A and 12B, a conductive film 1226 included in the pixel circuit 200 is electrically connected to the conductive film 1211 serving as the first wiring 211 (RS). A conductive film 1227 included in the pixel circuit 200 is electrically connected to the conductive film 1212 serving as the second wiring 212 (TX).

The conductive films 1213, 1218, 1222, 1225, 1226, and 1227 can be formed by processing one conductive film formed over an insulating surface into desired shapes. A gate insulating film 1228 is formed over the conductive films 1213, 1218, 1222, 1225, 1226, and 1227. The conductive films 1211, 1212, 1214, 1215, 1219, 1220, 1223, and 1224 can be formed by processing one conductive film formed over the gate insulating film 1228 into desired shapes.

An insulating film 1281 and an insulating film 1282 are formed over the conductive films 1211, 1212, 1214, 1215, 1219, 1220, 1223, and 1224. The conductive film 1221 is formed over the insulating film 1281 and the insulating film 1282.

An oxide semiconductor is preferably used for a semiconductor layer 1250 of the first transistor 201. In order that electrical charges generated by irradiation of the photodiode 220 with light are retained for a long time, the first transistor 201 electrically connected to the charge accumulation portion needs to be a transistor with an extremely small off-state current. Thus, the use of an oxide semiconductor material for the semiconductor layer 1250 improves the performance of the pixel circuit 200. Note that the charge accumulation portion is the wiring 205 in the pixel circuit 200 and corresponds to the conductive film 1220 in FIGS. 12A and 12B.

Figure 13A:
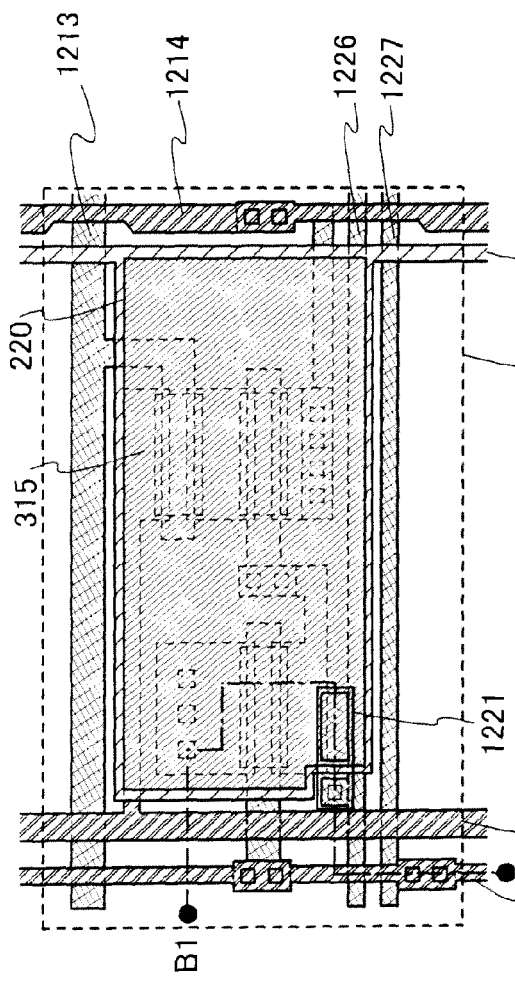
FIGS. 13A and 13B are respectively a top view and a cross-sectional view of a layout of a pixel circuit.
Figure 13B:
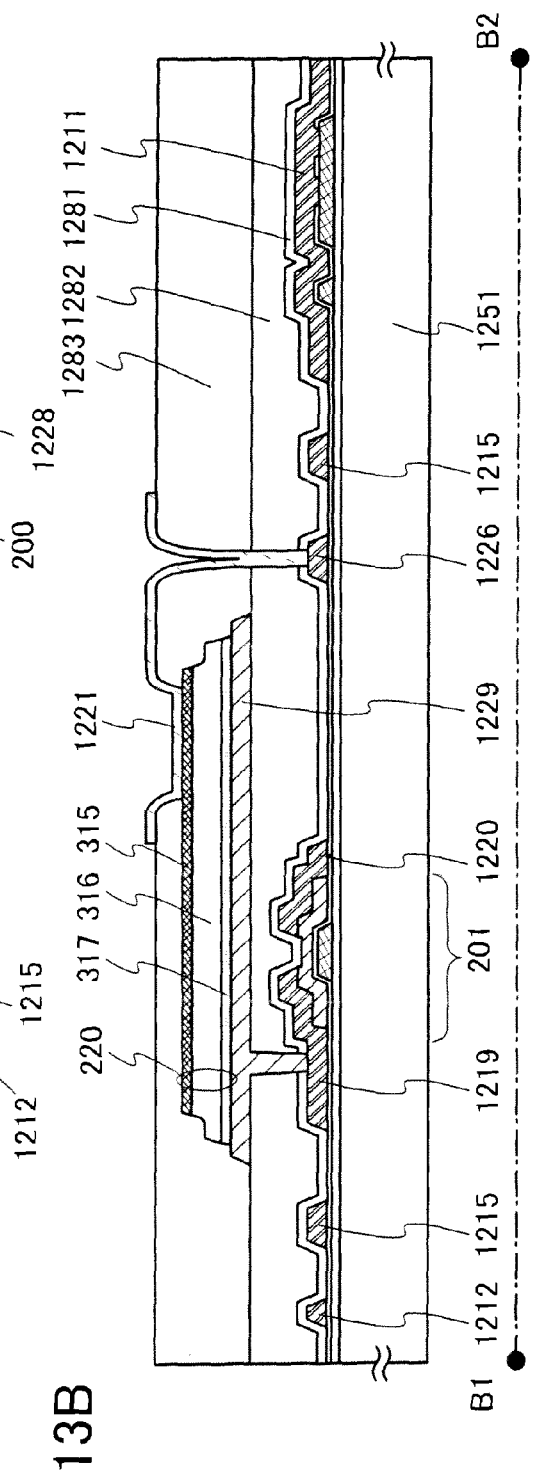

Further, the pixel circuit 200 may have a configuration in which an element such as a transistor overlaps with the photodiode 220 as illustrated in FIGS. 13A and 13B. Such a configuration increases the density of the pixels and the resolution of the imaging device. In addition, the area of the photodiode 220 can be increased, resulting in an increase in the sensitivity of the imaging device. FIG. 13A is a top view of the pixel circuit 200 and FIG. 13B is a cross-sectional view taken along the dashed line B1-B2 in FIG. 13A.

In the pixel circuit 200 illustrated in FIGS. 13A and 13B, the conductive film 1219 serving as one of the source electrode and the drain electrode of the first transistor 201 is electrically connected to the n-type semiconductor film 317 serving as the cathode of the photodiode 220 through the a conductive film 1229. The p-type semiconductor film 315 serving as the anode of the photodiode 220 is electrically connected to the conductive film 1226 in contact with the first wiring 211, through the conductive film 1221. An insulating film 1283 is formed to protect the photodiode 220. Except for the above and the element such as the transistor overlapping with the photodiode 220, the configuration of the pixel circuit in FIGS. 13A and 13B is similar to that of the pixel circuit 200 in FIGS. 12A and 12B.

Note that although a configuration in which the p-type semiconductor film 315 is directly electrically connected to the conductive film 1226 through the conductive film 1221 is shown as an example, another conductive film electrically connected to the conductive film 1226 through an opening formed in the insulating films 1281, 1282, and 1283 may be provided to be electrically connected to the conductive film 1221.

The configuration in which an element such as a transistor overlaps with an optical sensor element as illustrated in FIGS. 13A and 13B can also be applied to the pixel circuit 210 illustrated in FIG. 2B, the pixel circuits 250 and 260 illustrated in FIGS. 4A and 4B, and the pixel circuit 280 illustrated in FIG. 5.

This embodiment can be freely combined with any of the other embodiments in this specification.

(Embodiment 3)

In this embodiment, a transistor with an extremely small off-state current, which can be used for any of the pixel circuits described in Embodiments 1 and 2, and a material for the transistor are described.

As the structure of the transistor, FIGS. 12A and 12B and FIGS. 13A and 13B illustrate the top views and the cross-sectional views of the first transistor 201 including the semiconductor layer 1250. Although the transistor having a channel-etched bottom gate structure is shown as an example, the transistor may have a channel-protective bottom gate structure, a non-self-aligned top gate structure, or a self-aligned top gate structure.

To form the transistor with an extremely small off-state current, a semiconductor material having a wider band gap and lower intrinsic carrier density than a silicon semiconductor, such as an oxide semiconductor, is preferably used for the semiconductor layer 1250.

As one example of the semiconductor material, a compound semiconductor such as silicon carbide (SiC) or gallium nitride (GaN) can be given in addition to an oxide semiconductor. The oxide semiconductor has an advantage of high mass productivity because the oxide semiconductor can be formed by a sputtering method or a wet process, unlike silicon carbide or gallium nitride. Further, the oxide semiconductor can be formed even at room temperature; thus, the oxide semiconductor can be formed over a glass substrate or over an integrated circuit using silicon. Further, a larger substrate can be used. Accordingly, among the semiconductors with wide band gaps, the oxide semiconductor particularly has an advantage of high mass productivity. Further, in the case where an oxide semiconductor with high crystallinity is to be obtained in order to improve the property of a transistor (e.g., field-effect mobility), the oxide semiconductor with crystallinity can be easily obtained by heat treatment at 250° C. to 800° C.

Further, the conductivity type of a highly purified oxide semiconductor (purified OS) obtained by reduction of impurities such as moisture or hydrogen which serves as an electron donor (donor) and by reduction of oxygen vacancies is an i-type or a substantially i-type. Therefore, a transistor including the oxide semiconductor has a characteristic of a very small off-state current. Furthermore, the band gap of the oxide semiconductor is 2 eV or more, preferably 2.5 eV or more, more preferably 3 eV or more. With the use of an oxide semiconductor film which is highly purified by a sufficient decrease in the concentration of impurities such as moisture or hydrogen and reduction of oxygen vacancies, the off-state current of a transistor can be decreased.

Specifically, various experiments can prove a small off-state current of a transistor including a channel formation region formed of a highly-purified oxide semiconductor film. For example, even when an element has a channel width of $1\times10^6$ μm and a channel length of 10 μm, off-state current can be less than or equal to the measurement limit of a semiconductor parameter analyzer, i.e., less than or equal to $1\times10^{-13}$ A, at voltage (drain voltage) between a source electrode and a drain electrode of from 1 V to 10 V. In this case, it can be seen that the off-state current standardized on the channel width of the transistor is lower than or equal to 100 zA/μm. In addition, a capacitor and a transistor are connected to each other and the off-state current is measured with a circuit in which electrical charges flowing into or from the capacitor is controlled by the transistor. In the measurement, a purified oxide semiconductor film has been used for a channel formation region of the transistor, and the off-state current of the transistor has been measured from a change in the amount of electrical charge of the capacitor per unit time. As a result, it is found that in the case where the voltage between the source electrode and the drain electrode of the transistor is 3 V, a smaller off-state current of several tens of yoctoamperes per micrometer (yA/μm) can be obtained. Accordingly, the off-state current of the transistor including a channel formation region formed of the highly purified oxide semiconductor film is considerably smaller than that of a transistor including silicon having crystallinity.

Note that the oxide semiconductor preferably contains at least indium (In) or zinc (Zn). In particular, In and Zn are preferably contained. In addition, as a stabilizer for reducing the variation in electrical characteristics of a transistor using the oxide semiconductor, the oxide semiconductor preferably contains gallium (Ga) in addition to In and Zn. Tin (Sn) is preferably contained as a stabilizer. Hafnium (Hf) is preferably contained as a stabilizer. Aluminum (Al) is preferably contained as a stabilizer.

As another stabilizer, one or more of lanthanoids such as lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), or lutetium (Lu) may be contained.

As the oxide semiconductor, for example, indium oxide, tin oxide, zinc oxide, an In—Zn-based oxide, a Sn—Zn-based oxide, an Al—Zn-based oxide, a Zn—Mg-based oxide, a Sn—Mg-based oxide, an In—Mg-based oxide, an In—Ga-based oxide, an In—Ga—Zn-based oxide (also referred to as IGZO), an In—Al—Zn-based oxide, an In—Sn—Zn-based oxide, a Sn—Ga—Zn-based oxide, an Al—Ga—Zn-based oxide, a Sn—Al—Zn-based oxide, an In—Hf—Zn-based oxide, an In—La—Zn-based oxide, an In—Ce—Zn-based oxide, an In—Pr—Zn-based oxide, an In—Nd—Zn-based oxide, an In—Sm—Zn-based oxide, an In—Eu—Zn-based oxide, an In—Gd—Zn-based oxide, an In—Tb—Zn-based oxide, an In—Dy—Zn-based oxide, an In—Ho—Zn-based oxide, an In—Er—Zn-based oxide, an In—Tm—Zn-based oxide, an In—Yb—Zn-based oxide, or an In—Lu—Zn-based oxide, an In—Sn—Ga—Zn-based oxide, an In—Hf—Ga—Zn-based oxide, an In—Al—Ga—Zn-based oxide, an In—Sn—Al—Zn-based oxide, an In—Sn—Hf—Zn-based oxide, or an In—Hf—Al—Zn-based oxide can be used. The above oxide semiconductor may include silicon.

Note that an In—Ga—Zn-based oxide, for example, means an oxide containing In, Ga, and Zn, and there is no limitation on the ratio of In, Ga, and Zn. The In—Ga—Zn-based oxide may contain a metal element other than In, Ga, and Zn. The In—Ga—Zn-based oxide has sufficiently high resistance when there is no electric field and thus off-state current can be sufficiently reduced. In addition, also having high field-effect mobility, the In—Ga—Zn-based oxide is suitable for a semiconductor material used in a semiconductor device.

For example, an In—Ga—Zn-based oxide with an atomic ratio of In:Ga:Zn=1:1:1 (=1/3:1/3:1/3) or In:Ga:Zn=2:2:1 (=2/5:2/5:1/5), or an oxide with an atomic ratio close to the above atomic ratios can be used. Alternatively, an In—Sn—Zn-based oxide with an atomic ratio of In:Sn:Zn=1:1:1 (=1/3:1/3:1/3), In:Sn:Zn=2:1:3 (=1/3:1/6:1/2), or In:Sn:Zn=2:1:5 (=1/4:1/8:5/8), or an oxide with an atomic ratio close to the above atomic ratios may be used.

However, the composition is not limited to those described above, and a material having an appropriate composition may be used depending on needed electric characteristics (such as mobility and threshold voltage). Further, it is preferable to appropriately set the carrier density, the impurity concentration, the defect density, the atomic ratio of a metal element and oxygen, the interatomic distance, the density, or the like in order to obtain necessary semiconductor characteristics.

For example, the oxide semiconductor film can be formed by a sputtering method using a target containing indium (In), gallium (Ga), and zinc (Zn). In the case where an In—Ga—Zn-based oxide semiconductor film is formed by a sputtering method, it is preferable to use a target of an In—Ga—Zn-based oxide with an atomic ratio of In:Ga:Zn=1:1:1, 4:2:3, 3:1:2, 1:1:2, 2:1:3, or 3:1:4. When the oxide semiconductor film is formed using an In—Ga—Zn-based oxide target having the aforementioned atomic ratio, a crystal is readily formed. The filling rate of the target containing In, Ga, and Zn is 90 or higher, preferably 95% or higher. With the use of the target with high filling rate, a dense oxide semiconductor film is formed.

In the case where an In—Zn-based oxide material is used as an oxide semiconductor, a target of the In—Zn-based oxide has a composition ratio of In:Zn=50:1 to 1:2 in an atomic ratio ($In_2O_3$:ZnO=25:1 to 1:4 in a molar ratio), preferably In:Zn=20:1 to 1:1 in an atomic ratio ($In_2O_3$:ZnO=10:1 to 1:2 in a molar ratio), further preferably In:Zn=1.5:1 to 15:1 in an atomic ratio ($In_2O_3$:ZnO=3:4 to 15:2 in a molar ratio). For example, in a target used for formation of an oxide semiconductor film including an In—Zn-based oxide which has an atomic ratio of In:Zn:O=X:Y:Z, the relation of Z>1.5X+Y is satisfied. The mobility can be improved by keeping the ratio of Zn within the above range.

In the case of forming an In—Sn—Zn-based oxide semiconductor film as the oxide semiconductor film by a sputtering method, it is preferred to use an In—Sn—Zn—O target containing In, Sn, and Zn at an atomic ratio of 1:1:1, 2:1:3, 1:2:2, or 20:45:35.

A structure of the oxide semiconductor film is described below.

Note that in this specification, a term "parallel" indicates that the angle formed between two straight lines is greater than or equal to −10° and less than or equal to 10°, and accordingly also includes the case where the angle is greater than or equal to −5° and less than or equal to 5°. In addition, a term "perpendicular" indicates that the angle formed between two straight lines is greater than or equal to 80° and less than or equal to 100°, and accordingly includes the case where the angle is greater than or equal to 85° and less than or equal to 95°.

In this specification, the trigonal and rhombohedral crystal systems are included in the hexagonal crystal system.

An oxide semiconductor film is classified roughly into a single-crystal oxide semiconductor film and a non-single-crystal oxide semiconductor film. The non-single-crystal oxide semiconductor film includes any of an amorphous oxide semiconductor film, a microcrystalline oxide semiconductor film, a polycrystalline oxide semiconductor film, a c-axis aligned crystalline oxide semiconductor (CAAC-OS) film, and the like.

The amorphous oxide semiconductor film has disordered atomic arrangement and no crystalline component. A typical example thereof is an oxide semiconductor film in which no crystal part exists even in a microscopic region, and the whole of the film is amorphous.

The microcrystalline oxide semiconductor film includes a microcrystal (also referred to as nanocrystal) with a size greater than or equal to 1 nm and less than 10 nm, for example. Thus, the microcrystalline oxide semiconductor film has a higher degree of atomic order than the amorphous oxide semiconductor film. Hence, the density of defect states of the microcrystalline oxide semiconductor film is lower than that of the amorphous oxide semiconductor film.

The CAAC-OS film is one of oxide semiconductor films including a plurality of crystal parts, and most of the crystal parts each fit inside a cube whose one side is less than 100 nm. Thus, there is a case where a crystal part included in the CAAC-OS film fits inside a cube whose one side is less than 10 nm, less than 5 nm, or less than 3 nm. The density of defect states of the CAAC-OS film is lower than that of the microcrystalline oxide semiconductor film. The CAAC-OS film is described in detail below.

In a transmission electron microscope (TEM) image of the CAAC-OS film, a boundary between crystal parts, that is, a grain boundary is not clearly observed. Thus, in the CAAC-OS film, a reduction in electron mobility due to the grain boundary is less likely to occur.

According to the TEM image of the CAAC-OS film observed in a direction substantially parallel to a sample surface (cross-sectional TEM image), metal atoms are arranged in a layered manner in the crystal parts. Each metal atom layer has a morphology reflected by a surface over which the CAAC-OS film is formed (hereinafter, a surface over which the CAAC-OS film is formed is referred to as a formation surface) or a top surface of the CAAC-OS film, and is arranged in parallel to the formation surface or the top surface of the CAAC-OS film.

On the other hand, according to the TEM image of the CAAC-OS film observed in a direction substantially perpendicular to the sample surface (plan TEM image), metal atoms are arranged in a triangular or hexagonal configuration in the crystal parts. However, there is no regularity of arrangement of metal atoms between different crystal parts.

From the results of the cross-sectional TEM image and the plan TEM image, alignment is found in the crystal parts in the CAAC-OS film.

A CAAC-OS film is subjected to structural analysis with an X-ray diffraction (XRD) apparatus. For example, when the CAAC-OS film including an $InGaZnO_4$ crystal is analyzed by an out-of-plane method, a peak appears frequently when the diffraction angle (2θ) is around 31°. This peak is derived from the (009) plane of the $InGaZnO_4$ crystal, which indicates that crystals in the CAAC-OS film have c-axis alignment, and that the c-axes are aligned in a direction substantially perpendicular to the formation surface or the top surface of the CAAC-OS film.

On the other hand, when the CAAC-OS film is analyzed by an in-plane method in which an X-ray enters a sample in a direction substantially perpendicular to the c-axis, a peak appears frequently when 2θ is around 56°. This peak is derived from the (110) plane of the $InGaZnO_4$ crystal. Here, analysis (φ scan) is performed under conditions where the sample is rotated around a normal vector of a sample surface as an axis (φ axis) with 2θ fixed at around 56°. In the case where the sample is a single-crystal oxide semiconductor film of $InGaZnO_4$, six peaks appear. The six peaks are derived from crystal planes equivalent to the (110) plane. On the other hand, in the case of a CAAC-OS film, a peak is not clearly observed even when φ scan is performed with 2θ fixed at around 56°.

According to the above results, in the CAAC-OS film having c-axis alignment, while the directions of a-axes and b-axes are different between crystal parts, the c-axes are aligned in a direction parallel to a normal vector of a formation surface or a normal vector of the top surface. Thus, each metal atom layer arranged in a layered manner observed in the cross-sectional TEM image corresponds to a plane parallel to the a-b plane of the crystal.

Note that the crystal part is formed concurrently with deposition of the CAAC-OS film or is formed through crystallization treatment such as heat treatment. As described above, the c-axis of the crystal is aligned in a direction parallel to a normal vector of a formation surface or a normal vector of the top surface of the CAAC-OS film. Thus, for example, in the case where a shape of the CAAC-OS film is changed by etching or the like, the c-axis might not be necessarily parallel to a normal vector of a formation surface or a normal vector of the top surface of the CAAC-OS film.

Further, the degree of crystallinity in the CAAC-OS film is not necessarily uniform. For example, in the case where crystal growth leading to the CAAC-OS film occurs from the vicinity of the top surface of the film, the degree of the crystallinity in the vicinity of the top surface is higher than that in the vicinity of the formation surface in some cases. Further, when an impurity is added to the CAAC-OS film, the crystallinity in a region to which the impurity is added is changed, and the degree of crystallinity in the CAAC-OS film varies depending on regions.

Note that when the CAAC-OS film with an $InGaZnO_4$ crystal is analyzed by an out-of-plane method, a peak of 2θ may also be observed at around 36°, in addition to the peak of 2θ at around 31°. The peak of 2θ at around 36° indicates that a crystal having no c-axis alignment is included in part of the CAAC-OS film. It is preferable that in the CAAC-OS film, a peak of 2θ appear at around 31° and a peak of 2θ do not appear at around 36°.

In a transistor using the CAAC-OS film, change in electric characteristics due to irradiation with visible light or ultraviolet light is small. Thus, the transistor has high reliability.

Note that the oxide semiconductor film may be a stacked film including two or more films of an amorphous oxide semiconductor film, a microcrystalline oxide semiconductor film, and a CAAC-OS film, for example.

For example, the CAAC-OS film is formed by a sputtering method using a polycrystalline oxide semiconductor sputtering target. When ions collide with the sputtering target, a crystal region included in the sputtering target might be separated from the target along an a-b plane; in other words, a sputtered particle having a plane parallel to an a-b plane (flat-plate-like sputtered particle or pellet-like sputtered particle) might be separated from the sputtering target. In that case, the flat-plate-like sputtered particle reaches a substrate while maintaining their crystal state, whereby the CAAC-OS film can be formed.

For the deposition of the CAAC-OS film, the following conditions are preferably used.

By reducing the amount of impurities entering the CAAC-OS film during the deposition, the crystal state can be prevented from being broken by the impurities. For example, impurities (e.g., hydrogen, water, carbon dioxide, or nitrogen) which exist in the deposition chamber may be reduced. Furthermore, impurities in a deposition gas may be reduced. Specifically, a deposition gas whose dew point is −80° C. or lower, preferably −100° C. or lower is used.

By increasing the substrate heating temperature during the deposition, migration of a sputtered particle is likely to occur after the sputtered particle reaches a substrate surface. Specifically, the substrate heating temperature during the deposition is higher than or equal to 100° C. and lower than or equal to 740° C., preferably higher than or equal to 200° C. and lower than or equal to 500° C. When the substrate heating temperature during the deposition is increased and the flat-plate-like sputtered particle reaches the substrate, migration occurs over the substrate, so that a flat plane of the sputtered particle is attached to the substrate.

Furthermore, it is preferable that the proportion of oxygen in the deposition gas be increased and the power be optimized in order to reduce plasma damage at the deposition. The proportion of oxygen in the deposition gas is 30 vol % or higher, preferably 100 vol %.

As an example of the sputtering target, an In—Ga—Zn—O compound target is described below.

The In—Ga—Zn—O compound target, which is polycrystalline, is made by mixing $InO_X$ powder, $GaO_Y$ powder, and $ZnO_Z$ powder in a predetermined molar ratio, applying pressure, and performing heat treatment at a temperature higher than or equal to 1000° C. and lower than or equal to 1500° C. Note that X, Y, and Z are each a given positive number. Here, the predetermined molar ratio of $InO_X$ powder to $GaO_Y$ powder and $ZnO_Z$ powder is, for example, 2:2:1, 8:4:3, 3:1:1, 1:1:1, 4:2:3, or 3:1:2. The kinds of powder and the molar ratio for mixing powder may be determined as appropriate depending on the desired sputtering target.

When a transistor including a channel formation region formed of the oxide semiconductor described in this embodiment is used, a pixel circuit operating in the global shutter system can be easily realized, which makes it possible to provide an imaging device with a small amount of X-rays emitted to an object.

This embodiment can be implemented in appropriate combination with the structures described in the other embodiments.

This application is based on Japanese Patent Application serial No. 2012-184295 filed with Japan Patent Office on Aug. 23, 2012, the entire contents of which are hereby incorporated by reference.

What is claimed is:

1. An imaging device comprising:
   a first transistor, a second transistor, a third transistor, each comprising:
     a gate electrode over an insulting surface;
     an gate insulating film over the gate electrode;
     an oxide semiconductor layer over the gate insulating film; and
     a first electrode and a second electrode over the oxide semiconductor layer,
   a first capacitor;
   a resistor;
   a second capacitor;
   an operational amplifier circuit;
   a first insulating film over at least the first transistor, the second transistor, the third transistor;
   an optical sensor element;
   a second insulating film over the first insulating film and the optical sensor element; and
   a scintillator over the second insulating film,
   wherein the first electrode of the first transistor is electrically connected to a first portion of the optical sensor element with a first wiring through an opening of the first insulating film and an opening of the second insulating film,
   wherein the second electrode of the first transistor is electrically connected to a gate of the second transistor and the first capacitor,
   wherein the first electrode of the second transistor is electrically connected to the first electrode of the third transistor,
   wherein the second electrode of the third transistor is electrically connected to the resistor,
   wherein the resistor is electrically connected to an inverting input terminal of the operational amplifier circuit, and
   wherein an output terminal of the operational amplifier circuit is electrically connected to the inverting input terminal through the second capacitor.

2. The imaging device according to claim 1, wherein a first potential and a second potential are applied to a second portion of the optical sensor element and the gate electrode of the first transistor substantially at the same time to reset a charge of the first capacitor.

3. The imaging device according to claim 1, wherein the oxide semiconductor layer includes indium, gallium, and zinc.

4. The imaging device according to claim 1, wherein the optical sensor element comprises an amorphous semiconductor.

5. The imaging device according to claim 1, wherein the first wiring is over the second insulating film.

6. An imaging device comprising:
   a first transistor, a second transistor, a third transistor, each comprising:
     a gate electrode over an insulting surface;
     an gate insulating film over the gate electrode;
     an oxide semiconductor layer over the gate insulating film; and
     a first electrode and a second electrode over the oxide semiconductor layer,
   a first capacitor;
   a resistor;
   a second capacitor;
   an operational amplifier circuit;
   a first insulating film over at least the first transistor, the second transistor, the third transistor;
   a photodiode;
   a second insulating film over the first insulating film and the photodiode; and
   a scintillator over the second insulating film,
   wherein the first electrode of the first transistor is electrically connected to an electrode of the photodiode with a first wiring through an opening of the first insulating film and an opening of the second insulating film,
   wherein the second electrode of the first transistor is electrically connected to a gate of the second transistor and the first capacitor, wherein the first electrode of the second transistor is electrically connected to the first electrode of the third transistor, wherein the second electrode of the third transistor is electrically connected to the resistor, wherein the resistor is electrically connected to an inverting input terminal of the operational amplifier circuit, and wherein an output terminal of the operational amplifier circuit is electrically connected to the inverting input terminal through the second capacitor.

7. The imaging device according to claim 6, wherein a first potential and a second potential are applied to a cathode of the photodiode and the gate electrode of the first transistor substantially at the same time to reset a charge of the first capacitor.

8. The imaging device according to claim 6, wherein the oxide semiconductor layer includes indium, gallium, and zinc.

9. The imaging device according to claim 6, wherein the photodiode comprises an amorphous semiconductor.

10. The imaging device according to claim 6, wherein the first wiring is over the second insulating film.

11. An imaging device comprising:
a first transistor, a second transistor, a third transistor, each comprising:
  a gate electrode over an insulting surface;
  an gate insulating film over the gate electrode;
  an oxide semiconductor layer over the gate insulating film; and
  a first electrode and a second electrode over the oxide semiconductor layer,
a resistor;
a capacitor;
an operational amplifier circuit;
a first insulating film over at least the first transistor, the second transistor, the third transistor;
an optical sensor element;
a second insulating film over the first insulating film and the optical sensor element; and
a scintillator over the second insulating film,
wherein the first electrode of the first transistor is electrically connected to a first portion of the optical sensor element with a first wiring through an opening of the first insulating film and an opening of the second insulating film,
wherein the second electrode of the first transistor is electrically connected to the gate electrode of the second transistor,
wherein the first electrode of the second transistor is electrically connected to the first electrode of the third transistor,
wherein the second electrode of the third transistor is electrically connected to the resistor,
wherein the resistor is electrically connected to an inverting input terminal of the operational amplifier circuit, and
wherein an output terminal of the operational amplifier circuit is electrically connected to the inverting input terminal through the capacitor.

12. The imaging device according to claim 11, wherein a first potential and a second potential are applied to a second portion of the optical sensor element and the gate electrode of the first transistor substantially at the same time to reset a charge between the second electrode of the first transistor and the gate electrode of the second transistor.

13. The imaging device according to claim 11, wherein the oxide semiconductor layer includes indium, gallium, and zinc.

14. The imaging device according to claim 11, wherein the optical sensor element comprises an amorphous semiconductor.

15. The imaging device according to claim 11, wherein the first wiring is over the second insulating film.

16. An imaging device comprising:
a first transistor, a second transistor, a third transistor, each comprising:
  a gate electrode over an insulting surface;
  an gate insulating film over the gate electrode;
  an oxide semiconductor layer over the gate insulating film; and
  a first electrode and a second electrode over the oxide semiconductor layer,
a resistor;
a capacitor;
an operational amplifier circuit;
a first insulating film over at least the first transistor, the second transistor, the third transistor;
a photodiode;
a second insulating film over the first insulating film and the photodiode; and
a scintillator over the second insulating film,
wherein the first electrode of the first transistor is electrically connected to an electrode of the photodiode with a first wiring through an opening of the first insulating film and an opening of the second insulating film,
wherein the second electrode of the first transistor is electrically connected to a gate of the second transistor,
wherein the first electrode of the second transistor is electrically connected to the first electrode of the third transistor,
wherein the second electrode of the third transistor is electrically connected to the resistor,
wherein the resistor is electrically connected to an inverting input terminal of the operational amplifier circuit, and
wherein an output terminal of the operational amplifier circuit is electrically connected to the inverting input terminal through the capacitor.

17. The imaging device according to claim 16, wherein a first potential and a second potential are applied to a cathode of the photodiode and the gate electrode of the first transistor substantially at the same time to reset a charge between the second electrode of the first transistor and the gate electrode of the second transistor.

18. The imaging device according to claim 16, wherein the oxide semiconductor layer includes indium, gallium, and zinc.

19. The imaging device according to claim 16, wherein the photodiode comprises an amorphous semiconductor.

20. The imaging device according to claim 16, wherein the first wiring is over the second insulating film.

* * * * *